(12) United States Patent
Widenhouse et al.

(10) Patent No.: US 8,328,761 B2
(45) Date of Patent: Dec. 11, 2012

(54) VARIABLE SURGICAL ACCESS DEVICE

(75) Inventors: Christopher W. Widenhouse, Clarksville, OH (US); Frederick E. Shelton, IV, Hillsboro, OH (US); Michael S. Cropper, Edgewood, KY (US); Mark Tsonton, Loveland, OH (US); Robert P. Gill, Mason, OH (US); James W. Voegele, Cincinnati, OH (US); Michael A. Murray, Bellevue, KY (US); Christopher J. Hess, Cincinnati, OH (US); William Bruce Weisenburgh, II, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 722 days.

(21) Appl. No.: 12/242,726

(22) Filed: Sep. 30, 2008

(65) Prior Publication Data

US 2010/0081995 A1  Apr. 1, 2010

(51) Int. Cl.
*A61M 5/178* (2006.01)
(52) U.S. Cl. .................................................. 604/164.08
(58) Field of Classification Search ............. 604/164.08, 604/167.06, 173, 164.09; 600/206
See application file for complete search history.

(56) References Cited

U.S. PATENT DOCUMENTS

| | | | |
|---|---|---|---|
| 2,129,391 A | 9/1938 | Wappler | |
| 3,402,710 A | 9/1968 | Paleschuck | |
| 3,654,965 A | 4/1972 | Gramain | |
| 4,112,932 A | 9/1978 | Chiulli | |
| 4,306,545 A | 12/1981 | Ivan et al. | |
| 4,402,683 A | 9/1983 | Kopman | |
| 4,417,888 A | 11/1983 | Cosentino et al. | |
| 5,183,464 A | 2/1993 | Dubrul et al. | |
| 5,183,471 A | 2/1993 | Wilk | |
| 5,197,955 A | 3/1993 | Stephens et al. | |
| 5,207,213 A | 5/1993 | Auhll et al. | |
| 5,209,737 A | 5/1993 | Ritchart et al. | |
| 5,209,741 A | 5/1993 | Spaeth | |
| 5,269,772 A | 12/1993 | Wilk | |
| 5,285,945 A | 2/1994 | Brinkerhoff et al. | |
| 5,308,336 A | 5/1994 | Hart et al. | |
| 5,320,611 A | 6/1994 | Bonutti et al. | |
| 5,330,437 A | 7/1994 | Durman | |
| 5,366,478 A | 11/1994 | Brinkerhoff et al. | |
| 5,366,748 A | 11/1994 | Villagran et al. | |
| 5,385,553 A | 1/1995 | Hart et al. | |
| 5,385,560 A | 1/1995 | Wulf | |
| 5,391,154 A | 2/1995 | Young | |
| 5,395,367 A | 3/1995 | Wilk | |
| 5,431,676 A | 7/1995 | Dubrul et al. | |

(Continued)

FOREIGN PATENT DOCUMENTS

EP      0568383      11/1993

(Continued)

OTHER PUBLICATIONS

U.S. Appl. No. 12/242,383, filed Sep. 30, 2008, Widenhouse, et al.

(Continued)

*Primary Examiner* — Nicholas Lucchesi
*Assistant Examiner* — Brooke Matney

(57) ABSTRACT

Various devices are provided for allowing multiple surgical instruments to be inserted through a single surgical access device at variable angles of insertion, allowing for ease of manipulation within a patient's body while maintaining insufflation. Safety shields and release mechanisms are also provided for use with various surgical access devices.

32 Claims, 42 Drawing Sheets

U.S. PATENT DOCUMENTS

| | | | |
|---|---|---|---|
| 5,443,452 A | 8/1995 | Hart et al. | |
| 5,443,484 A | 8/1995 | Kirsch et al. | |
| 5,480,410 A | 1/1996 | Cuschieri et al. | |
| 5,492,304 A | 2/1996 | Smith et al. | |
| 5,496,280 A | 3/1996 | Vandenbroek et al. | |
| 5,545,179 A | 8/1996 | Williamson, IV | |
| 5,569,205 A | 10/1996 | Hart et al. | |
| 5,569,254 A | 10/1996 | Carlson et al. | |
| 5,584,850 A | 12/1996 | Hart et al. | |
| 5,634,911 A | 6/1997 | Hermann et al. | |
| 5,634,937 A | 6/1997 | Mollenauer et al. | |
| 5,643,301 A | 7/1997 | Mollenauer | |
| 5,653,705 A | 8/1997 | de la Torre et al. | |
| 5,672,168 A | 9/1997 | de la Torre et al. | |
| 5,676,657 A | 10/1997 | Yoon | |
| 5,695,448 A | 12/1997 | Kimura et al. | |
| 5,752,970 A | 5/1998 | Yoon | |
| 5,814,058 A | 9/1998 | Carlson et al. | |
| 5,827,319 A | 10/1998 | Carlson et al. | |
| 5,865,807 A | 2/1999 | Blake, III | |
| 5,891,013 A | 4/1999 | Thompson | |
| 5,906,577 A | 5/1999 | Beane et al. | |
| 5,957,913 A | 9/1999 | de la Torre et al. | |
| 5,989,223 A | 11/1999 | Chu et al. | |
| 5,990,382 A | 11/1999 | Fox | |
| 5,997,515 A | 12/1999 | de la Torre et al. | |
| 6,004,303 A | 12/1999 | Peterson | |
| 6,024,736 A | 2/2000 | de la Torre et al. | |
| 6,066,090 A | 5/2000 | Yoon | |
| 6,077,288 A | 6/2000 | Shimomura et al. | |
| 6,086,603 A | 7/2000 | Termin et al. | |
| 6,120,513 A | 9/2000 | Bailey et al. | |
| 6,123,689 A | 9/2000 | To et al. | |
| 6,162,196 A * | 12/2000 | Hart et al. | 604/167.02 |
| 6,217,555 B1 | 4/2001 | Hart et al. | |
| 6,245,052 B1 | 6/2001 | Orth et al. | |
| 6,254,534 B1 | 7/2001 | Butler et al. | |
| 6,258,069 B1 | 7/2001 | Carpentier et al. | |
| 6,277,064 B1 | 8/2001 | Yoon | |
| 6,315,770 B1 | 11/2001 | de la Torre et al. | |
| 6,319,246 B1 | 11/2001 | de la Torre et al. | |
| 6,328,730 B1 | 12/2001 | Harkrider, Jr. | |
| 6,348,034 B1 | 2/2002 | Thompson | |
| 6,352,503 B1 | 3/2002 | Matsui et al. | |
| 6,440,061 B1 | 8/2002 | Wenner et al. | |
| 6,447,489 B1 | 9/2002 | Peterson | |
| 6,454,783 B1 | 9/2002 | Piskun | |
| 6,458,077 B1 | 10/2002 | Boebel et al. | |
| 6,551,270 B1 | 4/2003 | Bimbo et al. | |
| 6,551,282 B1 | 4/2003 | Exline et al. | |
| 6,589,167 B1 | 7/2003 | Shimomura et al. | |
| 6,605,063 B2 | 8/2003 | Bousquet | |
| 6,613,038 B2 | 9/2003 | Bonutti et al. | |
| 6,669,674 B1 | 12/2003 | Macoviak et al. | |
| 6,702,787 B2 | 3/2004 | Racenet et al. | |
| 6,706,033 B1 | 3/2004 | Martinez et al. | |
| 6,706,050 B1 | 3/2004 | Giannadakis | |
| 6,807,965 B1 | 10/2004 | Hickle | |
| 6,905,057 B2 | 6/2005 | Swayze et al. | |
| 6,908,430 B2 | 6/2005 | Caldwell et al. | |
| 6,939,296 B2 | 9/2005 | Ewers et al. | |
| 6,945,932 B1 | 9/2005 | Caldwell et al. | |
| 6,972,026 B1 | 12/2005 | Caldwell et al. | |
| 7,014,628 B2 | 3/2006 | Bousquet | |
| 7,052,454 B2 | 5/2006 | Taylor | |
| 7,083,626 B2 | 8/2006 | Hart et al. | |
| 7,118,528 B1 | 10/2006 | Piskun | |
| 7,163,510 B2 | 1/2007 | Kahle et al. | |
| 7,201,734 B2 | 4/2007 | Hickle | |
| 7,214,185 B1 | 5/2007 | Rosney et al. | |
| 7,247,154 B2 | 7/2007 | Hickle | |
| 7,338,473 B2 | 3/2008 | Campbell et al. | |
| 7,344,547 B2 | 3/2008 | Piskun | |
| 7,393,322 B2 | 7/2008 | Wenchell | |
| 7,413,559 B2 | 8/2008 | Stubbs et al. | |
| 7,540,839 B2 | 6/2009 | Butler et al. | |
| 7,850,600 B1 * | 12/2010 | Piskun | 600/114 |
| 2002/0156432 A1 | 10/2002 | Racenet et al. | |
| 2003/0028179 A1 | 2/2003 | Piskun | |
| 2003/0139756 A1 | 7/2003 | Brustad | |
| 2004/0015185 A1 | 1/2004 | Ewers et al. | |
| 2004/0073090 A1 | 4/2004 | Butler et al. | |
| 2004/0106942 A1 | 6/2004 | Taylor et al. | |
| 2004/0138528 A1 | 7/2004 | Richter et al. | |
| 2004/0199181 A1 | 10/2004 | Knodel et al. | |
| 2004/0204682 A1 * | 10/2004 | Smith | 604/167.06 |
| 2004/0215063 A1 | 10/2004 | Bonadio et al. | |
| 2004/0230160 A1 | 11/2004 | Blanco | |
| 2004/0230161 A1 | 11/2004 | Zeiner | |
| 2004/0254426 A1 | 12/2004 | Wenchell | |
| 2005/0020884 A1 | 1/2005 | Hart et al. | |
| 2005/0033342 A1 | 2/2005 | Hart et al. | |
| 2005/0059865 A1 | 3/2005 | Kahle et al. | |
| 2005/0070946 A1 | 3/2005 | Franer et al. | |
| 2005/0085842 A1 | 4/2005 | Eversull et al. | |
| 2005/0137609 A1 | 6/2005 | Guiraudon | |
| 2005/0148823 A1 | 7/2005 | Vaugh et al. | |
| 2005/0155611 A1 | 7/2005 | Vaugh et al. | |
| 2005/0192483 A1 | 9/2005 | Bonadio et al. | |
| 2005/0209608 A1 | 9/2005 | O'Heeron | |
| 2005/0222582 A1 | 10/2005 | Wenchell | |
| 2005/0267419 A1 | 12/2005 | Smith | |
| 2005/0273132 A1 | 12/2005 | Shluzas et al. | |
| 2005/0277946 A1 | 12/2005 | Greenhalgh | |
| 2006/0019592 A1 | 1/2006 | Kupferberg et al. | |
| 2006/0019723 A1 | 1/2006 | Vorenkamp et al. | |
| 2006/0020241 A1 | 1/2006 | Piskun et al. | |
| 2006/0020281 A1 | 1/2006 | Smith | |
| 2006/0024500 A1 | 2/2006 | Seo | |
| 2006/0025652 A1 | 2/2006 | Vargas | |
| 2006/0071432 A1 | 4/2006 | Staudner | |
| 2006/0212062 A1 | 9/2006 | Farascioni | |
| 2006/0224129 A1 | 10/2006 | Beasley et al. | |
| 2006/0224164 A1 | 10/2006 | Hart et al. | |
| 2006/0229501 A1 | 10/2006 | Jensen et al. | |
| 2006/0241651 A1 | 10/2006 | Wilk | |
| 2006/0241671 A1 | 10/2006 | Greenhalgh | |
| 2006/0247500 A1 | 11/2006 | Voegele et al. | |
| 2006/0247673 A1 | 11/2006 | Voegele et al. | |
| 2006/0264706 A1 | 11/2006 | Piskun | |
| 2006/0271075 A1 | 11/2006 | Bilotti et al. | |
| 2007/0049966 A1 | 3/2007 | Bonadio et al. | |
| 2007/0060939 A1 | 3/2007 | Lancial et al. | |
| 2007/0085232 A1 | 4/2007 | Brustad et al. | |
| 2007/0088202 A1 | 4/2007 | Albrecht et al. | |
| 2007/0088277 A1 | 4/2007 | McGinley et al. | |
| 2007/0118021 A1 | 5/2007 | Pokorney | |
| 2007/0151566 A1 | 7/2007 | Kahle et al. | |
| 2007/0185453 A1 | 8/2007 | Michael et al. | |
| 2007/0208312 A1 | 9/2007 | Norton et al. | |
| 2007/0255218 A1 | 11/2007 | Franer | |
| 2007/0255219 A1 | 11/2007 | Vaugh et al. | |
| 2007/0260121 A1 | 11/2007 | Bakos et al. | |
| 2007/0260273 A1 | 11/2007 | Cropper et al. | |
| 2008/0027476 A1 | 1/2008 | Piskun | |
| 2008/0051739 A1 | 2/2008 | McFarlane | |
| 2008/0065021 A1 | 3/2008 | Jenkins et al. | |
| 2008/0119821 A1 | 5/2008 | Agnihotri et al. | |
| 2008/0255519 A1 | 10/2008 | Piskun et al. | |
| 2008/0287877 A1 * | 11/2008 | Gresham et al. | 604/167.06 |
| 2009/0005799 A1 | 1/2009 | Franer et al. | |
| 2009/0227843 A1 * | 9/2009 | Smith et al. | 600/208 |
| 2010/0081863 A1 | 4/2010 | Hess et al. | |
| 2010/0081864 A1 | 4/2010 | Hess et al. | |
| 2010/0081871 A1 | 4/2010 | Widenhouse et al. | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0228094 A1 | 9/2010 | Ortiz et al. | |

FOREIGN PATENT DOCUMENTS

| | | |
|---|---|---|
| EP | 0646358 | 4/1995 |
| EP | 950376 | 10/1999 |
| EP | 1350476 | 10/2003 |
| EP | 1716813 A1 | 11/2006 |

| | | |
|---|---|---|
| EP | 1731105 | 12/2006 |
| EP | 2098182 A2 | 9/2009 |
| FR | 2710270 | 3/1995 |
| JP | 2006320750 | 11/2006 |
| WO | WO-0217800 A2 | 3/2002 |
| WO | 2005087112 | 9/2005 |
| WO | 2005094432 | 10/2005 |
| WO | 2006019592 | 2/2006 |
| WO | 2006019723 | 2/2006 |
| WO | 2006035446 | 4/2006 |
| WO | 2007119232 | 10/2007 |
| WO | 2008024502 | 2/2008 |
| WO | 2008093313 | 8/2008 |
| WO | WO-2008121294 A1 | 10/2008 |
| WO | 2008149332 | 12/2008 |
| WO | WO-2009035663 A2 | 3/2009 |

OTHER PUBLICATIONS

U.S. Appl. No. 12/242,333, filed Sep. 30, 2008, Hess, et al.
U.S. Appl. No. 12/242,353, filed Sep. 30, 2008, Hess, et al.
U.S. Appl. No. 12/242,381, filed Sep. 30, 2008, Murray, et al.
U.S. Appl. No. 12/242,765, filed Sep. 30, 2008, Widenhouse, et al.
U.S. Appl. No. 12/242,711, filed Sep. 30, 2008, Murray, et al.
U.S. Appl. No. 12/242,721, filed Sep. 30, 2008, Hess, et al.
European Search Report for EP 09 25 2312 dated Feb. 25, 2010. ( 5 pages).
Product Brochure "Access the Future of Laparoscopic Surgery" Advanced Surgical Concepts Limited, Inc.
Ahmad G, Duffy JM, Phillips K, Watson A., " Laparoscopic Entry Techniques" Cochrane Database Syst Rev., (2): CD006583, Apr. 16, 2008.
European Search Report for Application No. 09252291, dated Jan. 19, 2010. (5 pages).
European Search Report for Application No. 09252296, dated Feb. 4, 2010. (7 pages).
European Extended Search Report for Application No. 09252291.1, dated Apr. 23, 2010 (9 pages).
European Extended Search Report for Application No. 09252312.5, dated Jun. 10, 2010 (11 pages).
European Search Report for Application No. 09252313.3, dated Jan. 19, 2010. (5 pages).
Gill IS, Canes D, Aron M, Haber GP, Goldfarb DA, Flechner S, Desai MR, Kaouk JH, Desai MM., "Single Port Transumbilical (E-Notes) Donor Nephrectomy" Journal Urol., 180(2):637-41; Aug. 2008.
Bucher P, Pugin F, Morel P., "Single Port Access Laparoscopic Right Hemicolectomy" Int J Colorectal Dis., Jul. 8, 2008.
Canes D, Desai MM, Aron M, Haber GP, Goel RK, Stein RJ, Kaouk JH, Gill IS., "Transumbilical Single-Port Surgery: Evolution and Current Status" Eur Urol., Jul. 14, 2008.
Goel RK, Kaouk JH., "Single Port Access Renal Cryoablation (SPARC): A New Approach" Eur Urol. Jun. 2008;53 (6):1204-9. Epub Mar. 18, 2008.
Kaouk JH, Palmer JS., "Single-port Laparoscopic Surgery: Initial Experience in Children for Varicocelectomy" BJU Int.;102(1):97-9. Epub Mar. 5, 2008.
Ponsky LE, Cherullo EE, Sawyer M, Hartke D., "Single Access Site Laparoscopic Radical Nephrectomy: Initial Clinical Experience" J Endourol., 22(4):663-6, Apr. 2008.
Ponsky TA, Lukish JR., "Single Site Laparoscopic Gastrostomy with a 4-mm Bronchoscopic Optical Grasper" J Pediatric Surgery, 43(2):412-4, Feb. 2008.
Rane A, Rao P, Rao P. Single-port-access Nephrectomy and Other Laparoscopic Urologic Procedures Using a Novel Laparoscopic Port (R-port), Urology. (2):260-3; discussion, Epub May 12, 2008.
Kaouk JH, Haber GP, Goel RK, Desai MM, Aron M, Rackley RR, Moore C, Gill IS., "Single-port Laparoscopic Surgery in Urology: lniitial Experience", Urology., 71(1):3-6., Jan. 2008.
Vassallo C, Berbiglia G, Pessina A, Carena M, Firullo A, Griziotti A, Ramajoli F, Palamarciuc E, Fariseo M. "The Super-Magenstrasse and Mill Operation with Pyloroplasty: Preliminary Results", Obesity Surgery, 17, Aug. 2007.
Johnston D , Dachtler J , Sue-Ling HM, King RF, Martin I. G, Roderick F.G. "The Magenstrasse and Mill Operation for Morbid Obesity" Obesity Surgery, Apr. 2003.
K. Sumiyama, C. Gostout, E.Rajan, T.Bakken, M.Knipschield, S.Chung, P.Cotton, R.Hawes, A.Kalloo, A.Kalloo, S. Kantsevoy and P.Pasricha "Transgastric Cholecystectomy: Transgastric Accessibility to the Gallbladder Improved with the SEMF Method and a Novel Multibending Therapeutic Endoscope" Gastrointestinal Endoscopy, vol. 65, Issue 7, Jun. 2007.
Web Page www.websurg.com/notes/videos.php <http://www.websurg.com/notes/videos.php>, Screenshots videos "Notes Hybrid Sleeve Gastrectomy Performed During Course" Vix, MD; Solano, MD; Asakuma, MD, Feb. 2008.
Web Page www.websurg.com/notes/videos.php <http://www.websurg.com/notes/videos.php>, Screenshots videos "Transvaginal Hybrid Notes Sleeve Gastrectomy Porcine Model" Vix, MD; Solano, MD; Asakuma, MD, Dec. 2007.
Ahmad G, Duffy JM, Phillips K, Watson A., "Laparoscopic Entry Techniques" Cochrane Database Syst Rev., (2): CD006583, Apr. 16, 2008.

* cited by examiner

VARIABLE SURGICAL ACCESS DEVICE

FIELD OF THE INVENTION

The present invention relates to surgical access devices for providing surgical access into a body cavity.

BACKGROUND OF THE INVENTION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through a the trocar sleeve. Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. Instruments used for mini-laparoscopic procedures are, however, generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedures. In addition, smaller 2-3 mm incisions may still cause undesirable cosmetic outcomes and wound complications (bleeding, infection, pain, keloid formation, etc.).

Since the benefits of smaller and fewer body cavity incisions are proven, it would be desirable to perform an operation utilizing only a single incision in the navel. An umbilicus is well-hidden and the thinnest and least vascularized area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems which allow laparoscopic procedures to be performed entirely through the umbilicus or a surgical port located elsewhere while at the same time reducing or eliminating the "chopstick effect."

SUMMARY OF THE INVENTION

The present invention generally provides devices for allowing surgical access to an interior of a patient's body. In one embodiment, a surgical access device is provided and can include a retractor having an opening extending therethrough for forming a pathway through tissue into a body cavity. A housing can be coupled to the retractor and can define a longitudinal axis extending therethrough. The housing can include a plurality of rigid sealing ports in communication with the opening in the retractor. In some embodiments, each sealing port can have a sealing element therein and can having a central axis that forms an angle with the longitudinal axis of the housing that is greater than zero. The central axis of each sealing port can be different than the central axis of every other sealing port.

In one exemplary embodiment, at least one of the sealing ports can have an opening with a diameter different than a diameter of an opening in the other sealing ports. The sealing ports can be rotatable relative to the housing and two or more sealing ports can be rotatable as a unit with respect to the housing. Each sealing element can be configured for lateral and pivotal movement and can be freely movable relative to the housing such that the angular orientation of the central axis is adjustable. In one embodiment, an adapter can be removably matable to at least one of the sealing ports to change an effective diameter of the sealing port. In other embodiments, the adapter can have a non-circular cross-section to receive and form a seal with a surgical instrument having a non-circular cross-section.

While the housing can have any configuration, in one embodiment, the housing is movable between a convex configuration and a concave configuration. The housing can be rotatable relative to the retractor. A flexible connector, for example a bellows, can extend between the housing and the retractor to allow the housing to move polyaxially relative to the retractor. In some embodiments, the housing can be hingedly connected to the retractor. The retractor can include a proximal flange and a distal flange having a flexible cylindrical portion extending therebetween. The housing can include a distal annulus that releasably couples to the proximal flange of the retractor. The surgical access device can also include a release mechanism configured to allow selective engagement and disengagement of the housing with the retractor.

In another exemplary embodiment, the surgical access device can include a flexible shield disposed within the retractor and configured to protect the retractor from damage caused by insertion of surgical instruments through the sealing ports and the retractor. The retractor can optionally include a lighting element disposed thereon to allow illumination of a body cavity.

In another embodiment, a surgical access device is provided and can include a housing having a plurality of rigid sealing ports with sealing elements therein for receiving surgical instruments. The plurality of sealing ports can have central axes extending therethrough that differ from one another. In some embodiments, the central axes of the sealing ports can be different than a central longitudinal axis of the housing and at least one of the sealing ports can be rotatable relative to the housing.

The surgical access device can further include a flexible cannula extending distally from the housing for receiving surgical instruments inserted through the sealing ports. In one exemplary embodiment, the housing can be rotatable relative to the flexible cannula. The housing can optionally be flexible and movable between a convex configuration and concave configuration to allow reorientation of the central axes of the sealing ports.

In other aspects, a surgical access device is provided and can include a housing having a plurality of sealing ports. Each sealing port can have a seal with a non-circular opening configured to form a seal around an instrument having a non-circular cross-section, and each seal can be rotatable relative to the housing to allow the seal to rotate with and maintain a seal around an instrument inserted therethrough. In some embodiments, each seal can have a different non-circular opening shape, and the non-circular opening in at least one of the seals can have a shape that can include, but is not limited to, triangular, quadrilateral, and oval. The surgical access device can further include a retractor extending from the housing that can have an opening formed therethough for receiving surgical instruments. The housing can be rotatable relative to the retractor, and the seals can float relative to the retractor.

In another exemplary embodiment, a surgical access device is provided and can include a retractor having an opening extending therethrough and a housing coupled to the retractor and having a plurality of sealing ports. The housing can be freely rotatable relative to the retractor to allow positioning of surgical instruments through the sealing ports during use. The sealing ports can optionally be positioned non-symmetrically within the housing. The surgical access device can also include a base ring disposed between the retractor and the housing and configured to allow rotation of the housing. A release mechanism can be releasably mated to the retractor and the housing and can be configured to allow decoupling of the housing from the retractor. In some embodiments, at least one of the sealing ports can be oriented to have a central axis different than a central longitudinal axis of the housing and the retractor, and at least one of the sealing ports can be rotatable relative to the housing. In addition, at least one sealing port can have a seal element that extends in a plane that forms an angle with a central longitudinal axis of the housing, and the angle between the plane and the central longitudinal axis of the housing can be adjustable.

In another exemplary embodiment, a surgical access device is provided and can include a housing having a flexible cannula extending therefrom that can be configured for guiding a surgical instrument into a patient's body. A sealing element can be disposed within the housing and configured to receive a surgical instrument. The sealing element can be rotatable relative to the housing to allow a surgical device inserted through the sealing element and the flexible cannula to rotate therein without causing the flexible cannula to rotate. The sealing element can be disposed within an opening formed through the housing and can include at least one of an instrument seal for forming a seal around a surgical instrument and a channel seal for forming a seal in the opening when no instrument is inserted therethrough. In some embodiments, the surgical access device can further include steering cables coupled to the flexible cannula and configured to steer the flexible cannula along a tortuous pathway. A locking mechanism can also be included for locking rotational motion of the sealing element relative to the housing and the flexible cannula.

Various shields and collars can be used with the various embodiments of surgical access devices, and in one exemplary embodiment, a surgical access device is provided and can include a retractor having an opening extending therethrough for forming a pathway through tissue into a body cavity. A housing can be coupled to the retractor and can have a plurality of sealing ports for receiving surgical instruments. A flexible shield can be disposed within the retractor and it can be configured to protect tissue from damage caused by the insertion of surgical instruments through the sealing ports and the retractor. In some embodiments, the flexible shield can have a length at least as long as a length of the retractor. In other embodiments, the flexible shield can have a length that is greater than a length of the retractor.

The flexible shield can be coupled to the housing and can be configured to extend therefrom into a body cavity of a patient in which surgery is performed. Steering cables can be coupled to the flexible shield and configured to steer the flexible shield along a tortuous pathway. In one embodiment, the flexible shield can be removably coupled to the housing and can be formed from any suitable material known in the art including, but not limited to, silicone, urethane, thermoplastic elastomer, rubber, polyolefins, polyesters, nylons, and fluoropolymers. Each sealing port can have a central axis that differs from one another and that differs from a central longitudinal axis of the housing. The housing can be rotatable relative to the retractor and at least one of the sealing ports can be rotatable relative to the housing. In some embodiments, the surgical access device can further include a flexible connector extending between the housing and the retractor to allow the housing to move polyaxially relative to the retractor. As such, the flexible shield can extend through the flexible connector and the retractor.

In another exemplary embodiment, a surgical access device is provided and can include a housing having a plurality of sealing ports for receiving surgical instruments. A retractor can be positionable in an opening of a patient's body and can extend distally from the housing for receiving surgical instruments inserted through the sealing ports. A collar can extend proximally from the housing and can be configured to protect tissue from damage caused by insertion of surgical instruments advanced into the sealing ports of the housing. The collar can have a substantially conical shape with a distal opening and a proximal opening, and the distal opening can receive a base of the housing. In one embodiment, at least a distal portion of the collar is substantially rigid and can be formed of, for example, polycarbonate or high density polyethylene. In other embodiments, at least a proximal portion of the collar is substantially flexible and can be formed of, for example, silicone, urethane, thermoplastic elastomer, and rubber.

The collar can include a releasable securing element on a distal portion thereof for releasably securing the collar to the housing. In one embodiment, the securing element can be one or more cantilevered snaps. In addition, the collar can have a plurality of suture holes disposed around a proximal portion thereof for securing the collar to tissue. The housing can be rotatable relative to the retractor and rotation of the collar can be effective to rotate the housing. In some embodiments, the collar can include guide markings for orienting the housing and for guiding surgical instruments into the sealing ports.

In one exemplary embodiment, a surgical access device is provided and can include a base ring having a proximal facing surface and a distal facing surface, a retractor extending distally from the distal facing surface of the base ring, and a housing extending proximally from the proximal facing surface of the base ring. The housing can have a plurality of sealing ports, and a shield can extend distally from the base ring through an interior of the retractor. The shield can be configured to protect the retractor from damage caused by insertion of surgical instruments therethrough.

In some embodiments, the shield can be releasably coupled to the base ring and can have a length that is greater than a length of the retractor. Steering cables can be coupled to the flexible shield and configured to steer the flexible shield along a tortuous pathway. The surgical access device can also include a release mechanism for removing the collar from the base ring. In one embodiment, the surgical access device can include a plurality of shields extending distally from each of the plurality of sealing ports.

In another exemplary embodiment, a surgical access device is provided and can include a housing having a plurality of access ports. Each access port can include a seal element having a slit adapted for selectively opening and closing to seal the access port when no instrument is passed therethrough. In addition, each slit can extend substantially tangential to a circumference of the housing. At least one of the seal elements can have a maximum diameter when opened that is different than a maximum diameter of another one of the seal elements when opened.

In some embodiments, a proximal most portion of at least one of the seal elements can be flush with a proximal most portion of the housing. In other embodiments, a proximal most portion of at least one of the seal elements can be at a position proximal to a proximal most portion of the housing. In still further embodiments, a proximal most portion of at least one of the seal elements can be at a position distal to a proximal most portion of the housing. Each access port can have a central axis that differs from one another and at least one of the seal elements can be rotatable relative to the housing. In one embodiment, an adapter can be removably matable to at least one of the access ports to change an effective diameter of the access port. In addition, at least one of the access ports can include a second seal element having an opening with a non-circular shape for forming a seal around a surgical instrument with a non-circular cross-section.

The surgical access device can also include a retractor extending from the housing and having an opening for receiving surgical instruments inserted through the access ports. The housing can be rotatable relative to the retractor. The surgical access device can also include a flexible connector, for example a bellows, extending between the housing and the retractor to allow the housing to move polyaxially relative to the retractor. In one embodiment, the housing can be hingedly connected to the retractor by a flexible connector. The surgical access device can also include a release mechanism that selectively engages and disengages the housing and the retractor. A flexible shield can be disposed within the retractor and configured to protect the retractor from damage caused by insertion of surgical instruments through the access ports and the retractor. The retractor can include a lighting element disposed thereon to allow illumination of a body cavity.

In other aspects, a surgical access device is provided and can include a retractor having an opening extending therethrough for forming a pathway through tissue into a body cavity, a housing having a plurality of sealing ports, and a release mechanism configured to releasably mate the housing to the retractor. In some embodiments, the housing can include a base ring and the retractor can include a proximal flange. The release mechanism can engage the base ring and the proximal flange to mate the housing to the retractor. In one exemplary embodiment, the release mechanism can be a C-clamp selectively positionable around the base ring and the proximal flange to mate the housing with the retractor. The release mechanism can also be a latch formed on the proximal flange and configured to selectively engage and disengage the base ring. The release mechanism can take any form known in the art including, but not limited to, a push button, a switch, and a trigger. The release mechanism can also be effective to lock the housing in a desired rotational position.

In some embodiments, each sealing port can have an opening formed through the housing and can have at least one of an instrument seal for forming a seal around a surgical instrument inserted therethrough and a channel seal for forming a seal in the opening when no instrument is inserted therethrough. Each sealing port can have a central axis that differs from one another and at least one of the sealing ports can be rotatable relative to the housing. In other embodiments, the housing can be rotatable relative to the retractor. The surgical access device can also include a flexible shield disposed within the retractor and configured to protect the retractor from damage caused by insertion of surgical instruments through the sealing ports and the retractor. In addition, there can be a plurality of housings having a plurality of sealing ports and each housing can be interchangeable with the others.

In another exemplary embodiment, a surgical access device is provided and can include a housing having a plurality of access ports with duckbill seals extending distally therefrom and a retractor extending distally from the housing. A mid-portion of the retractor can have a diameter that is less than a diameter of the housing. The duckbill seals can be oriented to minimize unintentional contact by the retractor with the seals that would cause the seals to open. For example, each duckbill seal can include a slit configured to selectively open and close, and the slits can be oriented tangentially to a circumference of the housing.

In some embodiments, at least one of the access ports can have an opening with a diameter different than a diameter of an opening in the other access ports and each access port can have a central axis that differs from one another. In addition, at least one of the duckbill seals can be positioned distally to the other duckbill seals. In other embodiments, at least one of the duckbill seals can extend into the mid-portion of the retractor and at least one of the duckbill seals can be rotatable relative to the housing.

An adapter can be removably matable to at least one of the access ports to change an effective diameter of the access port. In one embodiment, at least one of the access ports can include an instrument seal having an opening with a non-circular shape configured to form a seal around a surgical instrument with a non-circular cross-section. In addition, the housing can be rotatable relative to the retractor. The surgical access device can further include a connector extending between the housing and the retractor to allow the housing to move relative to the retractor. A release mechanism can be configured to allow selective engagement and disengagement of the housing with the retractor. In some embodiments, a flexible shield can be disposed within the retractor and configured to protect the retractor from damage caused by insertion of surgical instruments through the access ports and the retractor.

In another exemplary embodiment, a surgical access device is provided and can include a housing having a flexible base with a plurality of rigid sealing ports extending therethrough that can have a sealing element therein. The flexible base can be movable to allow each sealing port to selectively position instruments extending through the sealing element at converging and diverging positions relative to one another. The flexible base can be movable between a convex configuration and a concave configuration. Each sealing port within the housing can be selectively movable between a proximal position within the housing and a distal position within the housing.

The surgical access device can also include a retractor extending distally from the housing and configured to form an opening through tissue for receiving instruments inserted through the sealing ports. The housing can include a distal annulus that releasably couples to a proximal flange on the retractor and can be rotatable relative to the retractor. In some embodiments, each sealing port can have a central axis that differs from one another and that differs from a central longitudinal axis of the housing. At least one of the sealing ports can have an opening with a diameter different than a diameter of an opening in the other sealing ports. In one exemplary embodiment, at least one of the sealing ports can have a non-circular opening and can be rotatable relative to the flexible base.

The surgical access device can also include a flexible connector extending between the housing and the retractor to allow the housing to move relative to the retractor, and the housing can be hingedly connected to the retractor. A release mechanism can be configured to allow selective engagement and disengagement of the housing with the retractor. In one embodiment, a flexible shield can be disposed within the retractor and configured to protect the retractor from damage caused by insertion of surgical instruments through the sealing ports and the retractor. The retractor can also include a lighting element disposed thereon to allow illumination of a body cavity. In some embodiments, each sealing port includes at least one of an instrument seal configured to form a seal around an instrument inserted therethrough and a channel seal configured to seal the access port when no instrument is inserted therethrough.

In another exemplary embodiment, a surgical access device is provided and can include a housing having a plurality of rigid sealing ports with sealing elements therein for receiving surgical instruments. Each sealing port can be individually movable independent of the housing such that each sealing port has a full range of lateral and vertical motion, and combinations thereof, relative to the housing. The plurality of sealing ports can be disposed in a flexible base that is movable between a convex configuration and a concave configuration. A retractor can extend distally from the housing and can be configured to form an opening through tissue for receiving instruments inserted through the sealing ports.

In one embodiment, the housing can include a distal annulus that releasably couples to a proximal flange on the retractor, and the housing can be rotatable relative to the retractor. Each sealing port can have a central axis that differs from one another and that differs from a central longitudinal axis of the housing. At least one of the sealing ports can have an opening with a diameter different than a diameter of an opening in the other sealing ports. In addition, at least one of the sealing ports can be rotatable relative to the housing. An adapter can be removably matable to at least one of the sealing ports to change an effective diameter of the sealing port.

The surgical access device can also include a flexible connector extending between the housing and the retractor to allow the housing to move relative to the retractor. A release mechanism can be configured to allow selective engagement and disengagement of the housing with the retractor. In other embodiments, a flexible shield can be disposed within the retractor and configured to protect the retractor from damage caused by insertion of surgical instruments through the sealing ports and the retractor.

In another embodiment, a surgical access device is provided and can include a housing having a retractor extending therefrom that can be configured to form a pathway through tissue. The housing can also include a plurality of rigid sealing ports having sealing elements therein for receiving surgical instruments therethrough. Each sealing element can be freely movable relative to one another, relative to the housing, and relative to tissue when the retractor is positioned in tissue. Each sealing element can be disposed in a flexible base coupled to the housing. In some embodiments, the flexible base can be movable between convex and concave positions to move the sealing ports. In other embodiments, each sealing element can freely move laterally, vertically, rotationally, and combinations thereof.

In one embodiment, the housing can be rotatable relative to the retractor and each sealing port can have a central axis that differs from one another and that differs from a central longitudinal axis of the housing. A connector can extend between the housing and the retractor to allow the housing to move relative to the retractor. The surgical access device can further include a release mechanism configured to allow selective engagement and disengagement of the housing with the retractor. A flexible shield can be disposed within the retractor and configured to protect the retractor from damage caused by insertion of surgical instruments through the sealing ports and the retractor.

In another exemplary embodiment, a surgical access device is provided and can include a housing having a plurality of sealing ports for receiving surgical instruments, a retractor having an opening formed therethrough for providing a pathway through tissue for surgical instruments inserted through the plurality of sealing ports, and a connector coupled between the housing and the retractor that can allow the housing to have a full range of lateral and vertical motion relative to the retractor. In some embodiments, the connector can allow rotational motion of the housing relative to the retractor and can have a proximal flange and a distal flange and a flexible cylindrical portion extending therebetween. While the connector can be formed of any suitable material known in the art, in one embodiment, the connector can be formed from an elastomeric material.

The housing can optionally be rotatable relative to the connector and at least one sealing port can be rotatable relative to the housing. Each sealing port can have a central axis that differs from one another and that differs from a central longitudinal axis of the housing. The surgical access device can also include a flexible shield disposed within the retractor and configured to protect the retractor from damage caused by insertion of surgical instruments through the sealing ports and the retractor.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
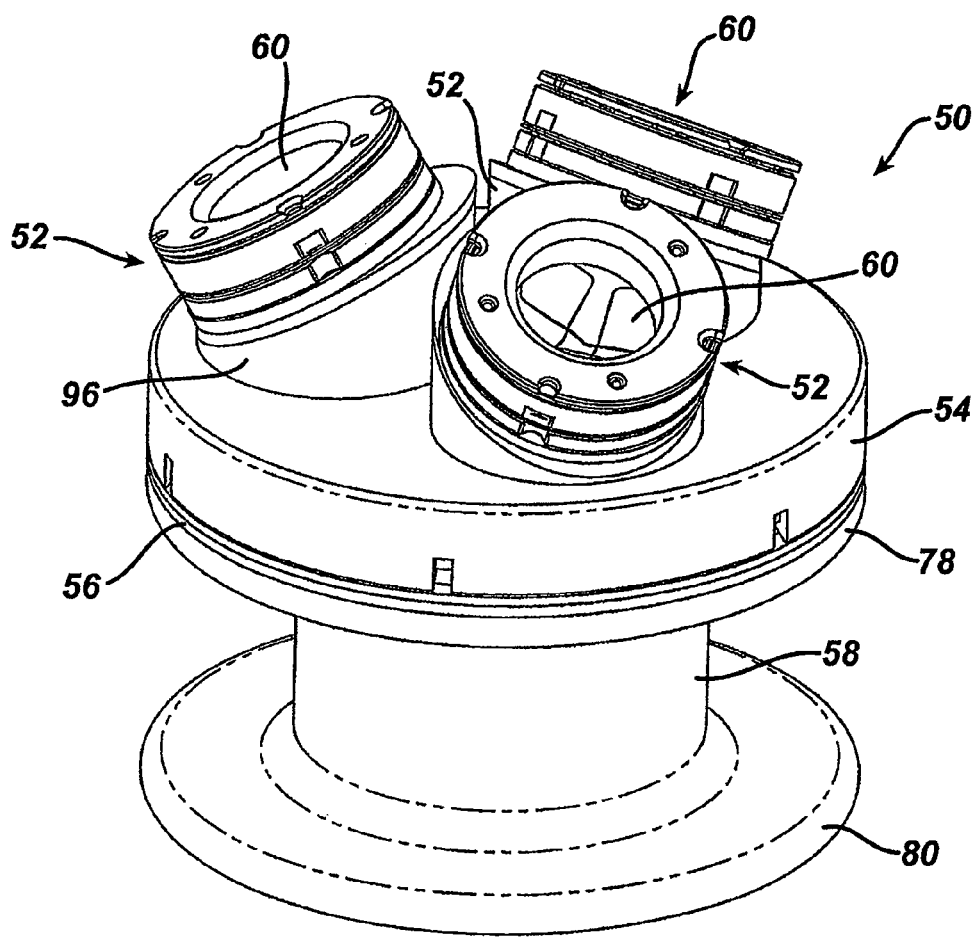
FIG. 1A is a perspective view of one embodiment of a surgical access device having a plurality of off-axis sealing ports extending therethrough.
Figure 1B:
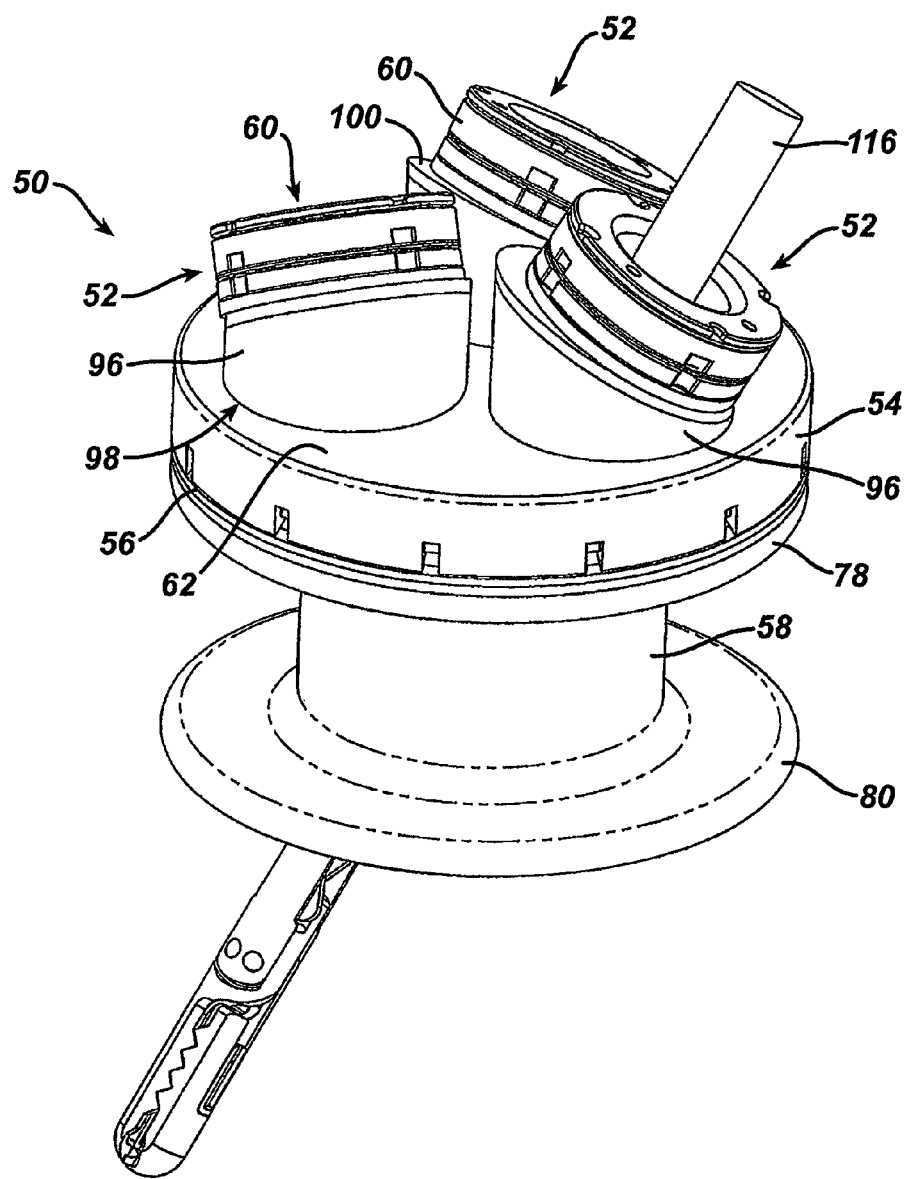
FIG. 1B is a perspective view of the surgical access device of FIG. 1A illustrating a surgical instrument extending through one of the sealing ports.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides improved surgical access devices that allow multiple surgical instruments to be inserted through a single surgical access device at variable angles of insertion, allowing for ease of manipulation within a patient's body while maintaining insufflation. In certain exemplary embodiments, a housing is provided having multiple access ports or sealing ports for receiving surgical instruments. Each sealing port can include one or more sealing elements therein for sealing the port and/or forming a seal around a surgical instrument disposed therethrough. The housing can define a central longitudinal axis, and the sealing ports can each have a central axis that is different from each other and different from the central longitudinal axis of the housing, thereby allowing a surgeon more control over the insertion of multiple surgical instruments. In some embodiments, the sealing ports and/or the sealing elements are capable of various types of movement, allowing the surgical instruments to be individually manipulated as needed.

The various surgical access devices can further include a wound protector, cannula, ring retractor, or other member for forming a pathway through tissue (hereinafter generally referred to as a retractor). The retractor can extend from the housing and it can be configured to be positioned within an opening in a patient's body. The sealing ports can each define working channels extending through the housing and aligned with the retractor. Any and all of the surgical access devices described herein can also include various other features, such as one or more ventilation ports to allow evacuation of smoke during procedures that utilize cautery and/or one or more insufflation ports through which the surgeon can insufflate the abdomen to cause pneumoperitenium, as described for example in U.S. Patent Application No. 2006/0247673 entitled "Multi-port Laparoscopic Access Device" filed Nov. 2, 2006 and incorporated herein by reference in its entirety. The insufflation port can be any size and can accept a leur lock or a needle, as will be appreciated by those skilled in the art.

Any and all embodiments of a surgical access device can also include one or more safety shields positioned through, in, and around any of the components and/or tissue to provide protection against puncture or tear by surgical instruments being inserted through the device. In addition, any and all embodiments of a surgical access device can include engagement and release mechanisms that allow certain components of the surgical access device to be removable as needed.

In use, the surgical access devices disclosed herein can be used to provide access to a patient's body cavity. The retractor can be positionable within an opening in a patient's body such that a distal portion of the retractor extends into a patient's body cavity and a proximal portion is coupled to a housing positioned adjacent to the patient's skin on an exterior of the patient's body. A lumen in the retractor can form a pathway through the opening in a patient's body so that surgical instruments can be inserted from outside the body to an interior body cavity. The elasticity of the skin of the patient can assist in the retention of the retractor in the body opening or incision made in the body. The retractor can be placed in any opening within a patient's body, whether a natural orifice or an opening made by an incision. For example, the retractor can be placed through the umbilicus, endoscopically including, vaginally, percutaneously, etc. In one embodiment, the retractor can be substantially flexible so that it can easily be maneuvered into and within tissue as needed. In other embodiments, the retractor can be rigid or semi-rigid. The retractor can be formed of any suitable material known in the art, for example silicone, urethane, thermoplastic elastomer, and rubber.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel created by the sealing port when no instrument is disposed therethrough; or a combination instrument seal and channel seal that is effective to both form a seal around an instrument disposed therethrough and to form a seal in the working channel when no instrument is disposed therethrough. A person skilled in the art will appreciate that various seals known in the art can be used including, for example, duckbill seals, cone seals, flapper valves, gel seals, diaphragm seals, lip seals, iris seals, etc. A person skilled in the art will also appreciate that any combination of seals can be included in any of the embodiments described herein, whether or not the seal combination are specifically discussed in the corresponding description of a particular embodiment.

Figure 1C:
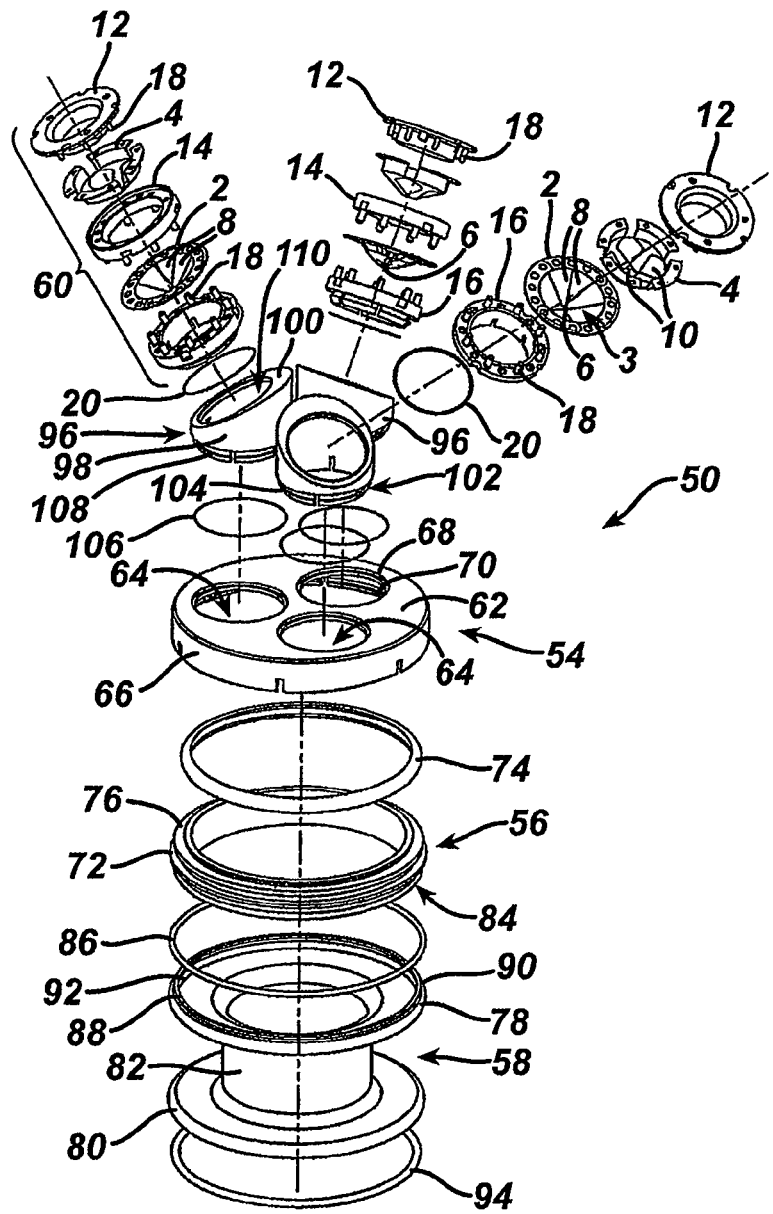
FIG. 1C is an exploded view of the surgical access device of FIG. 1A.
Figure 3A:
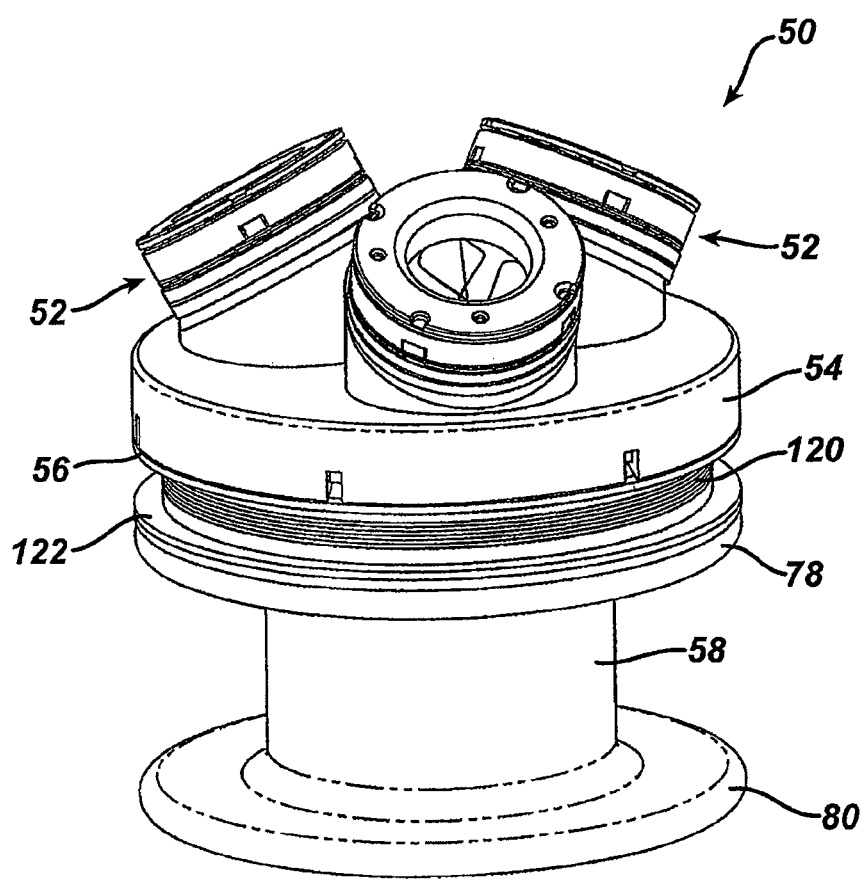
FIG. 3A is a perspective view of the surgical access device of FIG. 1A having a flexible connector in a compressed condition.
Figure 3B:
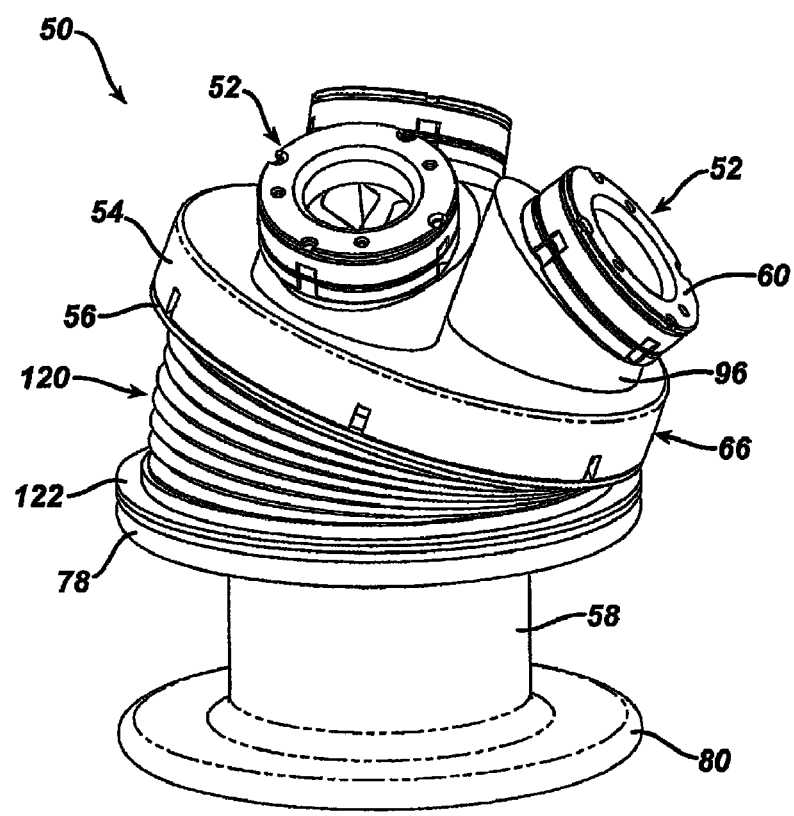
FIG. 3B is a perspective view of the surgical access device of FIG. 3A showing the flexible connector in an expanded configuration.
Figure 3C:
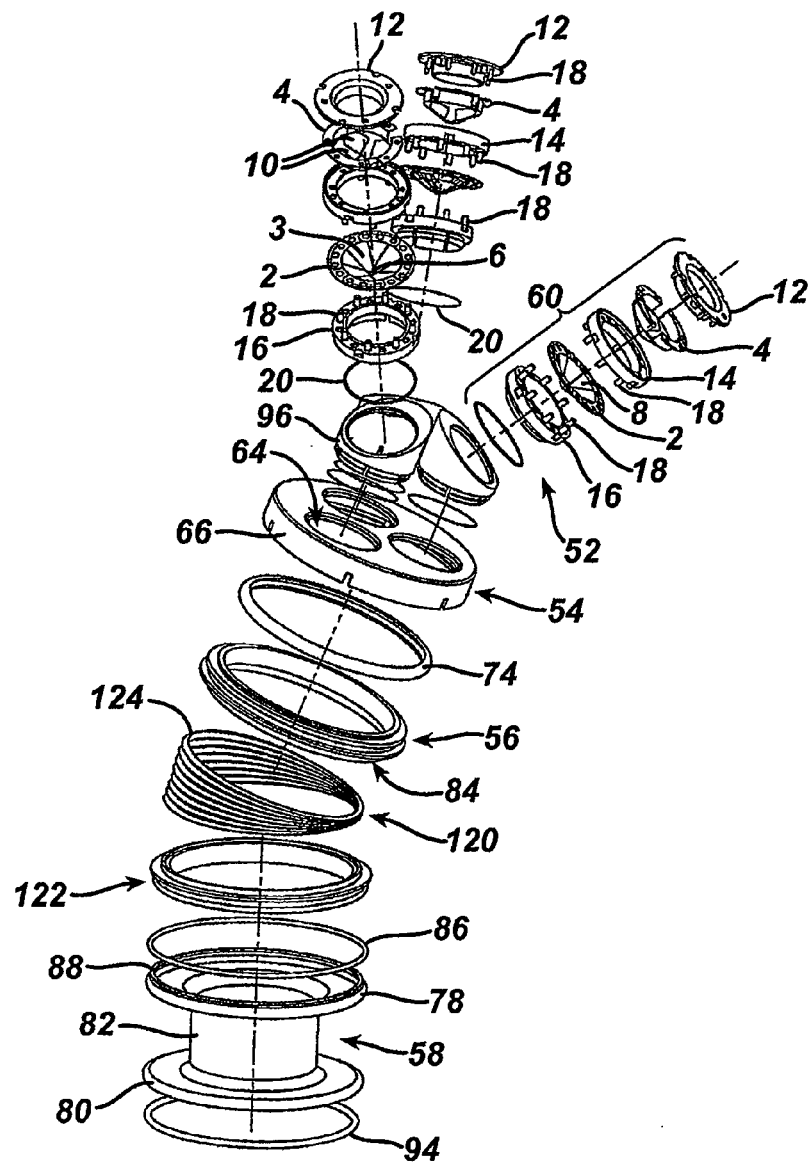
FIG. 3C is an exploded view of the surgical access device of FIG. 3A.
Figure 3D:
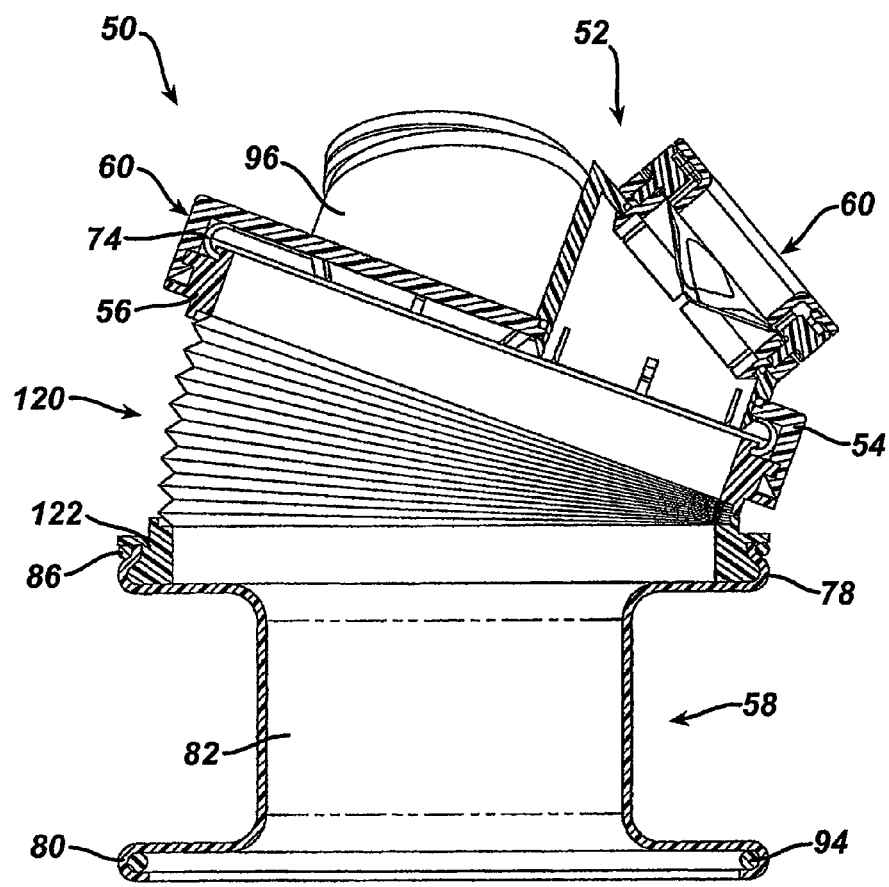
FIG. 3D is a cross-sectional view of the surgical access device of FIG. 3A.

In an exemplary embodiment, as shown in FIGS. 1C and 3C, a sealing element in the form of an instrument seal can generally have a multi-layer conical seal 2 and a multi-layer protective member 4 disposed on a proximal surface 3 of the conical seal 2. The multi-layer conical seal 2 can include a series of overlapping seal segments 8 that are assembled in a woven arrangement to provide a complete seal body. The seal segments 8 can be stacked on top of one another or woven together in an overlapping fashion to form the multi-layer seal 2 having a central opening 6 therein. The seal segments 8 can be made from any number of materials known to those skilled in the art, but in an exemplary embodiment the seal segments 8 are formed from an elastomeric material. The multi-layer protective member 4 can similarly be formed from a series of overlapping segments 10 that are disposed proximal to the overlapping seal segments 8 and that are configured to protect the seal segments 8 from damage caused by surgical instruments passed through the opening 6 in the seal 2. The protective member 4 can also be formed from various materials, but in certain exemplary embodiments the protective member 4 is formed from a molded thermoplastic polyurethane elastomer, such as Pellethane™.

The segments 8, 10 that form the seal 2 and the protective member 4 can be held together using various techniques known in the art. As shown in FIGS. 1C and 3C, the segments 8, 10 can be held together by several ring members that mate to engage the segments 8, 10 therebetween. In particular, the protective member 4 is engaged between a crown 12 and a gasket ring 14, and the seal 2 is engaged between the gasket ring 14 and a retainer ring 16. Pins 18 can be used to mate the ring members 12, 14, 16 and to extend through and engage the segments 8, 10 of the seal 2 and the protective member 4. In some embodiments, an o-ring 20 can be positioned between the retainer ring 16 and a sealing port housing to ensure an air and liquid tight seal between the same.

When fully assembled, the instrument seal can be disposed at various locations within the surgical access device. In some embodiments, the instrument seal can be disposed within sealing ports formed in the seal base of the surgical access device. In use, an instrument can be passed through a center opening of the instrument seal and the seal segments can engage and form a seal around an outer surface of the instrument to thereby prevent the passage of fluids and gas through the seal. When no instrument is disposed therethrough, the center opening will generally not form a seal in the working channel, however other configurations in which a seal is formed when no instrument is disposed therethrough are also conceivable. Exemplary instrument seal configurations are described in more detail in U.S. Publication No. 2004/0230161 entitled "Trocar Seal Assembly," filed on Mar. 31, 2004, and U.S. Publication No. 2007/0185453 entitled "Conical Trocar Seal," filed on Oct. 15, 2003, which are hereby incorporated by reference in their entireties.

Figure 1D:
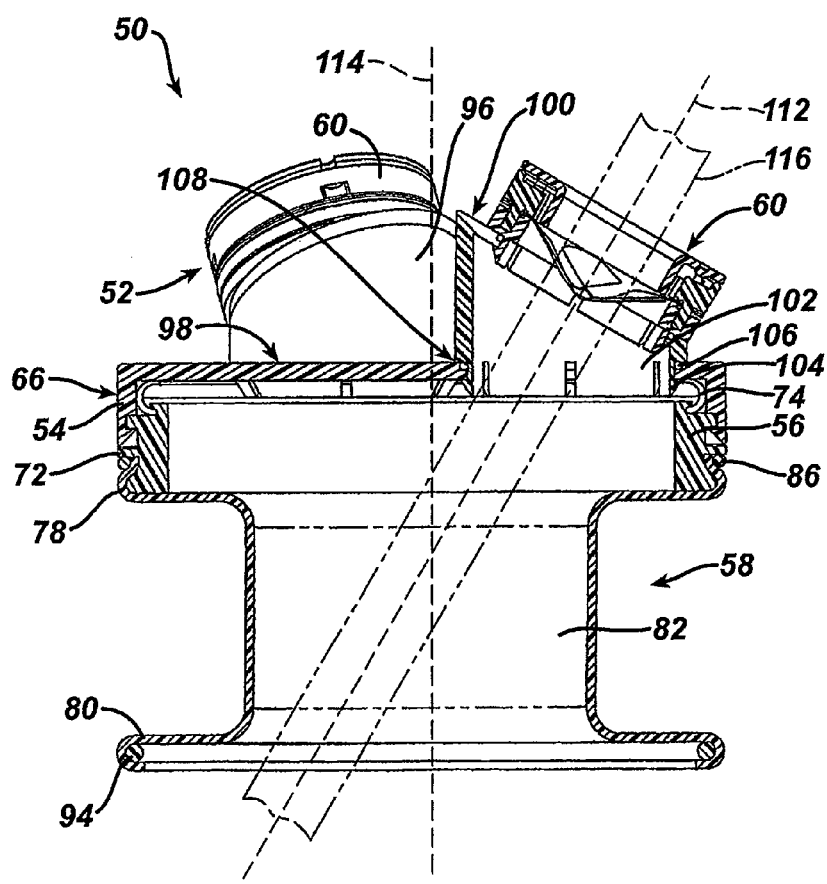
FIG. 1D is a cross-sectional view of the surgical access device and instrument of FIG. 1B.
Figure 1E:
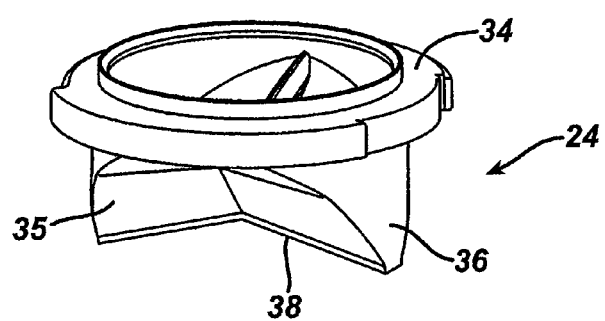
FIG. 1E is a perspective view of one embodiment of a duckbill sealing element for use in a surgical access device.

As noted above, another sealing element that can be used in the surgical access device is the channel or zero-closure seal, an example of which is shown in more detail in FIG. 1E. As shown, the illustrated zero-closure seal is in the form of a duckbill seal 24. The seal 24 is configured to form a seal in a working channel when no instrument is disposed therethrough to thus prevent the leakage of insufflation gases delivered through the surgical access device to the body cavity. As shown, the duckbill seal 24 can have a generally circular flange 34 with a sidewall 36 extending distally therefrom. The shape of the sidewall 36 can vary, but in the illustrated embodiment, the sidewall 36 includes opposed flaps 35 that extend at an angle toward one another in a distal direction and that come together at a distal end to form a seal face 38. In other embodiments, the opposed flaps 35 can extend toward one another with no angle to form a seal face 38 that is parallel relative to the circular flange 34. The opposed flaps 35 can be movable relative to one another to allow the seal face 38 to move between a closed position, in which no instrument is disposed therethrough and the seal face 38 seals the working channel of the surgical access device, and an open position in which an instrument is disposed therethrough. The seal can include various other features, as described in more detail in U.S. Publication No. 2009/0005799, entitled "Duckbill Seal with Fluid Drainage Feature," filed on Jun. 29, 2007, which is hereby incorporated by reference in its entirety. In addition, the seal face 38 of the seal 24 can be in any nonlinear shape or configuration known in the art, for example in an S-shaped configuration, as described in more detail in U.S. Pat. No. 5,330,437, entitled "Self Sealing Flexible Elastomeric Valve and Trocar Assembly for Incorporating Same," filed Nov. 12, 1993, which is hereby incorporated by reference in its entirety.

In accordance with the present disclosure the general structure of the seals do not generally form part of the present invention. As such, a person skilled in the art will certainly appreciate that any and all sealing elements and sealing configurations known in the art can be used within the surgical access device embodiments disclosed herein without departing from the spirit of the invention disclosed.

One particularly important aspect of the embodiments disclosed herein is that exemplary surgical access devices provide for greater maneuverability of surgical instruments within a patient while maintaining insufflation. In one embodiment, this greater maneuverability can be provided by having access or sealing ports extending through a seal base of a housing at various angles different from one another and different from a central longitudinal axis of the seal base and the housing. In other embodiments, this greater maneuverability can be provided by allowing for multi-directional movement of the various components of the device to thereby allow multi-directional movement of the surgical instruments disposed through the device. For example, components of the surgical access device that can allow for multi-directional movement can include, but are not limited to, sealing ports, access ports, sealing elements, seal bases, housings, retractors, and various other components that can be associated with the surgical access device and that will be described herein. Multi-directional movement as used herein can generally include rotational movement, vertical movement, lateral movement, angular movement, and any combinations thereof. Thus, any one of the various components of the surgical access device can generally have multi-directional movement relative to one or more of the various other components of the surgical access device and/or with respect to a patient's body, thereby allowing a multitude of ways surgical instruments can be moved and manipulated relative to and within a patient's body. It will be appreciated by those skilled in the art that any of the various aspects and features of the surgical access device embodiments described herein can be used in and applied to any and all of the various other embodiments, or to various devices known in the art.

In one embodiment shown in FIGS. 1A-1D, a surgical access device 50 is provided having a plurality of sealing ports 52 extending therethrough at various angular orientations. The surgical access device 50 can have a housing 56 with a seal base 54 that supports the sealing ports 52 and a retractor 58 extending from the housing 56. While any number of sealing ports 52 can be formed in the seal base 54, in the embodiment shown in FIG. 1A-1D, three sealing ports 52 extend through the surgical access device 50. The sealing ports 52 can have sealing elements 60 disposed therein, and the sealing ports 52 can be formed within the seal base 50 at various angles that are different from one another and different from a central longitudinal axis of the housing 56, as will be discussed in more detail below. Such a configuration can prevent interference between surgical instruments as they are inserted through the sealing ports 52 at various angular orientations, and can facilitate instrument positioning.

FIG. 1C illustrates the various components of the surgical access device 50. As shown, the housing 56 can be a substantially rigid cylindrical or circular member having outer threads 72 extending around an outer circumference thereof that are configured to threadedly mate with the inner threads 70 of the seal base 54, which forms the proximal portion of the housing 56. A housing o-ring 74, which can be flexible or rigid as needed, can be positioned on a top surface 76 of the housing 56 to form a seat and a seal between the housing 56 and the seal base 54. In one embodiment, the seal base 54 can be threadedly secured to the housing 56 via mating of the inner and outer threads 70, 72 such that the housing o-ring 74 is secured therebetween. The seal base 54 can have a proximal surface 62 with port openings 64 formed therethrough for receiving the sealing ports 52 and a circumferential wall 66 extending distally from the proximal surface 62. While any attachment or mating mechanism known in the art can be used to mate various components of the surgical access device 50 together, in the embodiment shown in FIGS. 1A-1D, an inner circumference of the port openings 64 can have inner threads 68 formed thereon to threadedly mate with the sealing ports 52. In addition, an inner circumference of the circumferential wall 66 can have inner threads 70 formed thereon to threadedly mate with the housing 56.

As noted above, the retractor 58 can extend from the housing 56, and in one embodiment, the retractor 58 is a substantially flexible member having a proximal flange 78 and a distal flange 80 with an inner elongate portion 82 extending therebetween. The proximal flange 78 can be configured to seat a distal rim 84 of the housing 56 and a proximal o-ring 86 can be positioned between the proximal flange 78 and the distal rim 84 of the housing 56. The distal rim 84 of the housing 56 can be attached to the proximal flange 78 of the retractor 58 and the proximal o-ring 86 by an adhesive, sealant, or any other attachment mechanism known in the art. In one embodiment, the proximal flange 78 can be mated to the housing 56 by a lip 88 extending proximally from an outer circumference thereof having threads 90 extending around an interior surface 92 thereof. The threads 90 can be configured to threadedly mate with the outer threads 72 on the housing 56 and thereby secure the retractor 58 to the housing 56. A distal o-ring 94 can optionally be positioned within the distal flange 80 of the retractor 58 to provide structural support to the retractor within a patient's body. The proximal and distal o-rings 86, 94 can be flexible or substantially rigid as needed for use in a particular application.

As noted above, any number of sealing ports 52 can be formed within and extend through the surgical access device 50. In general, each sealing port 52 can include a port housing 96, which can be seated within the port opening 64 in the seal base 54, and the sealing element 60 which can be positioned within the port housing 96. The port housing 96 can have any shape, height, or angular configuration known in the art as will be described in detail below, but in the embodiment shown in FIGS. 1A-1D, the port housing 96 can have a cylindrical shape. A distal surface 98 of the port housing 96 can be substantially flat such that it is coplanar with the proximal surface 62 of the seal base 54. A proximal surface 100 of the port housing 96 can likewise be flat, or it can extend at an angle with respect to the proximal surface 62 of the seal base 54. The angle at which the proximal surface 100 of the port housing 96 extends can determine the angular orientation of a longitudinal axis 112 of the sealing port 52, as will be discussed below. The distal surface 98 of the port housing can be mated to the seal base 54 using various mating techniques. As shown in FIG. 1C, the distal surface 98 has an extension portion 102 with deflectable members having a flange 104 formed around an exterior surface thereof for engaging the opening 64 in the seal base 54. The flange 104 can allow the port housing 96 to rotate, as will be discussed below. A port o-ring 106 can be placed within an aperture 108 extending around the extension portion 102 to facilitate sealing between the port housing 96 and the seal base 54 when the port housing 96 is threadedly mated with the opening in the housing 64. An opening 110 can extend through the port housing 96 for receiving the sealing element 60, for example an instrument seal.

As shown most clearly in FIG. 1D, because of the shape of the port housing 96, the sealing element 60 is positioned at an angle relative to the seal base 54 such that a central axis 112 of the sealing element 60, extending through a center portion thereof, is at an angle relative to a central longitudinal axis 114 of the seal base 54, housing 56, and the retractor 58. This allows a surgical instrument 116 to be inserted at varying angles as required in a particular procedure. In some embodiments, all of the sealing ports 52 can be configured to have central axes 112 different from each other. In other embodiments, two or more sealing ports 52 can have a central axis 112 that is the same relative to each other and different relative to a third, fourth, etc. sealing port 52.

As indicated above, in some embodiments the sealing ports 52 can be rotatable relative to the seal base 54. Rotation of the angled sealing ports 52 allows the axis 112 and thus the insertion angle provided by the sealing port 52 to be changed and adjusted. In this way, the sealing port 52 can be rotated prior to or after insertion of a surgical instrument therethrough to provide more space around an opening for manipulating the instrument and/or to enable better maneuverability of the instrument relative to tissue and to other instruments inserted through the access device.

Figure 2A:
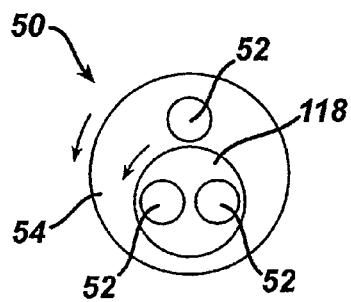
FIG. 2A is a top view of one embodiment of a surgical access device showing two sealing ports on a rotatable stage.
Figure 2B:
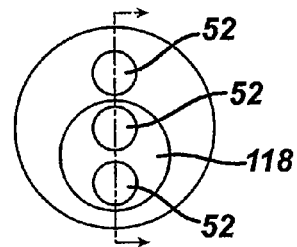
FIG. 2B is a top view of the surgical access device of FIG. 2A showing the rotatable stage in a rotated position.

In some embodiments, two or more sealing ports 52 can be positioned on a single rotatable stage 118, as shown in FIGS. 2A and 2B. The rotatable stage 118 can be a circular body that is rotatably disposed within a circular opening formed in the seal base 54. Various mating techniques, such as the extension with deflectable portions having a flange therearound as described above, can be used to allow rotation of the stage 118 within the opening in the seal base 54. In use, the stage 118 can allow the sealing ports 52 to be moved from a triangular configuration as shown in FIG. 2A, to an in-line configuration as shown in FIG. 2B, as well as any position therebetween. Rotating multiple sealing ports 52 at once can allow better maneuverability around the surgical access device 50 and/or can allow for repositioning of the surgical instruments while they are inserted within individual sealing ports 52. As will be appreciated by those skilled in the art, any number of sealing ports 52 can be formed in individual rotatable stages 118 on the seal base 54 to allow rotation of groups of sealing ports 52 relative to other sealing ports 52, the seal base 54, and/or the housing 56.

In other embodiments, the sealing ports 52 can be vertically, laterally, and angularly adjustable relative to the seal base 54 by forming at least a portion of the port housing 96 from a flexible connector, for example, a bellows. A flexible connector or bellows can allow the sealing element 60 positioned within the port housing 96 to be moved vertically, laterally, rotationally, and angularly as needed to adjust an insertion angle of a surgical instrument or a position of a surgical instrument within a body cavity.

In some embodiments, a connector 120 can be positioned between the housing 56 and the retractor 58, as shown in FIGS. 3A-3D. The connector 120 can generally be an element that allows movement of the housing 56 and the seal base 54 relative to the retractor 58. For example, the connector 120 can be a substantially flexible elongate portion and/or a bellows that allows the housing 56, and thereby the seal base 54 and the sealing ports 52, to have a full range of motion relative to the retractor 58. In one embodiment, the connector 120 can have a connector base 122 that seats the connector 120 and allows it to be mated with the proximal flange 78 of the retractor 58. A proximal portion 124 of the connector 120 can mate with the distal rim 84 of the housing 56 via any mating mechanism known in the art including, but not limited to, adhesive, sealant, threads, etc. In the same way, the connector base 122 and the connector 120 can be joined by any mating mechanism known in the art. In addition the connector base 122 can be threadedly or rotatably mated with the lip 88 of the retractor 58.

Figure 4A:
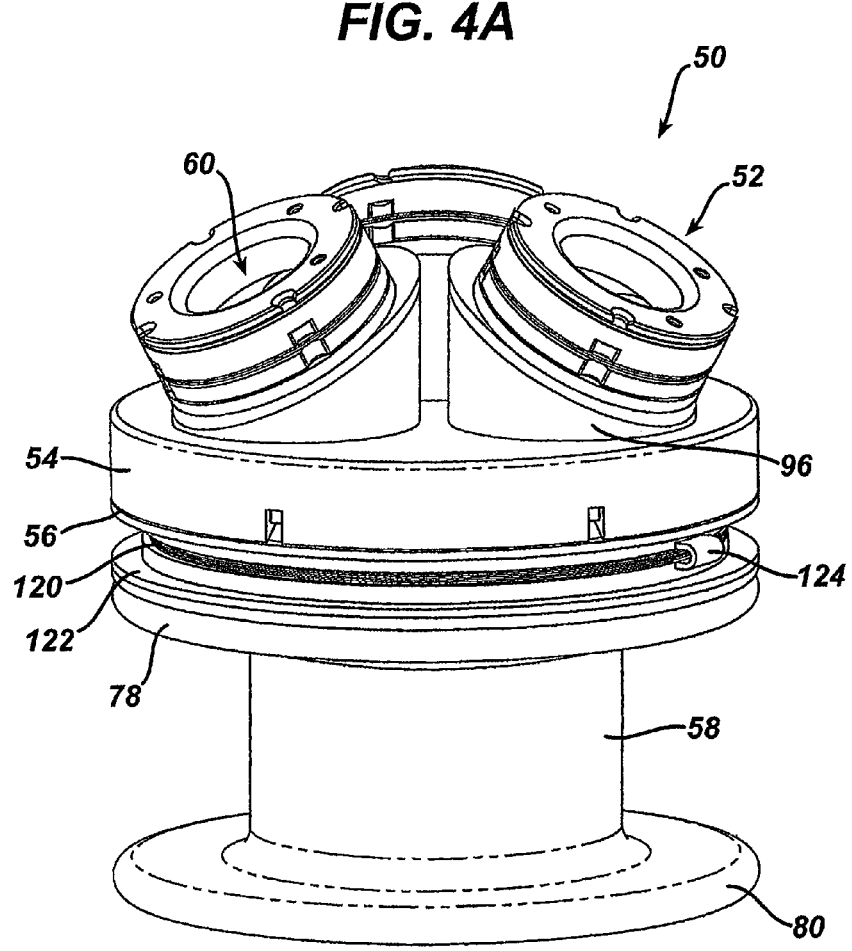
FIG. 4A is a perspective view of the surgical access device of FIG. 3A showing a hinge associated with the flexible connector.
Figure 4B:
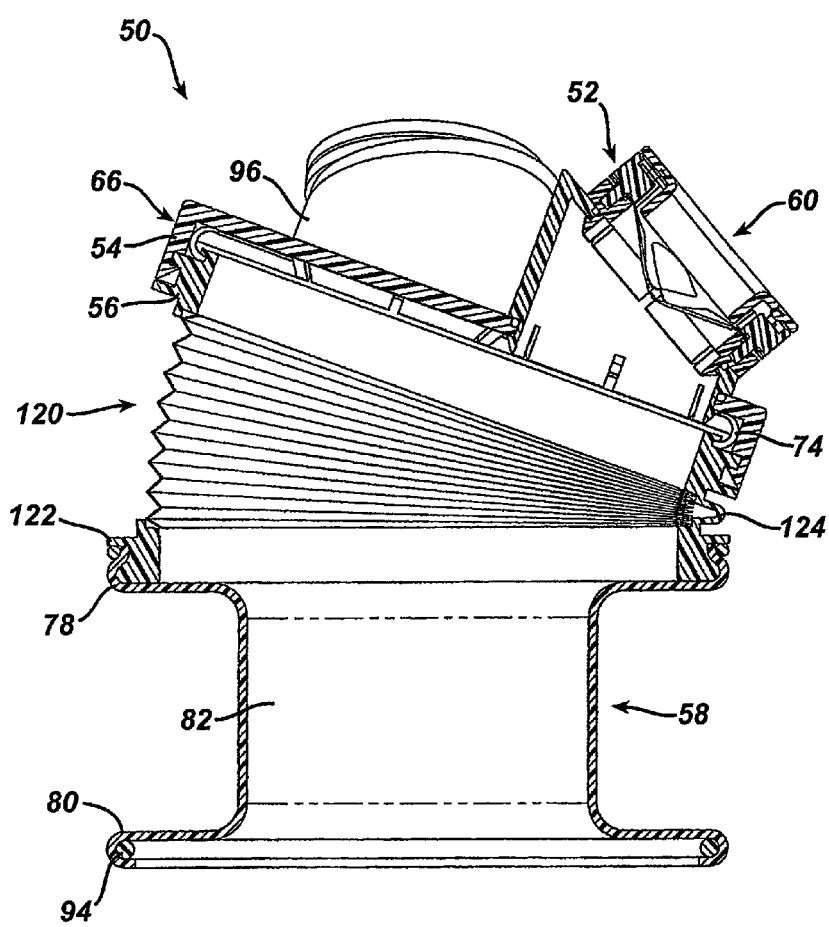
FIG. 4B is a cross-sectional view of the surgical access device of FIG. 4A showing the flexible connector in an expanded configuration.

In another embodiment shown in FIGS. 4A and 4B, a latch, living hinge, or clip 124 can be used to secure a portion of the connector 120 against movement, thereby allowing easier angular adjustment of the housing 56 and the seal base 54 relative to the retractor 58. As shown, the clip 124 can secure one side of the housing 56 to a corresponding side of the retractor 58, thereby allowing an opposing portion of the connector 120 to expand as it pivots about the connected point. In some embodiments, the connector 120 can be more flexible than the retractor 58 to ensure the retractor 58 remains secured within an opening in the body as the connector 120 is expanded and moved. As shown in FIG. 4B, any movement, whether vertical, lateral, rotational, or angular, allows the insertion angle and/or the position of the sealing ports 52 to be changed and adjusted relative to the retractor 58.

Figure 5A:
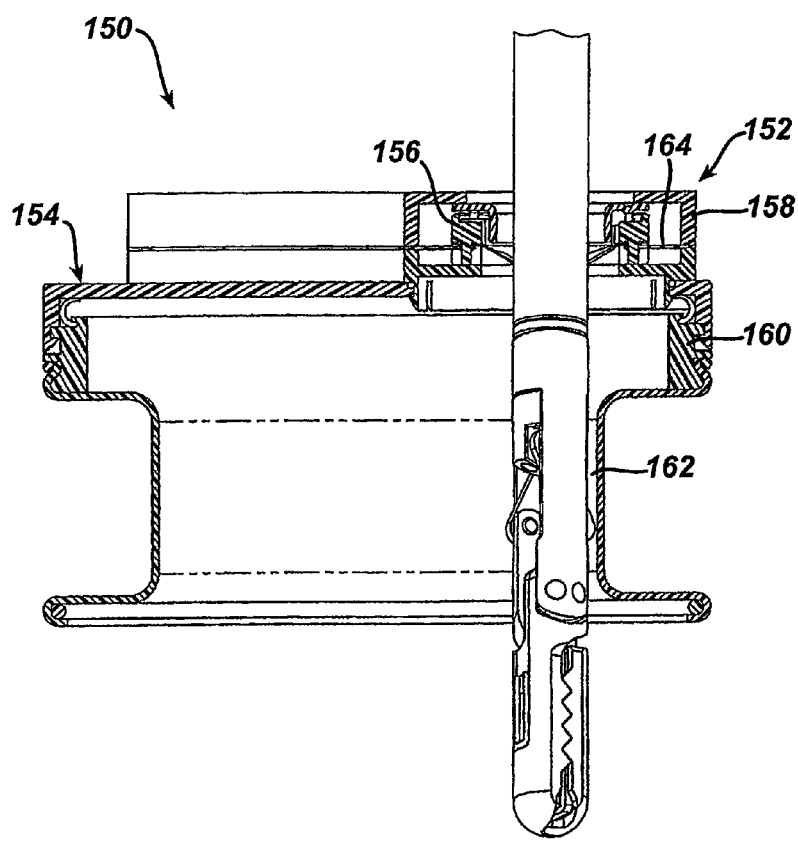
FIG. 5A is a partial cross-sectional view of one embodiment of a surgical access device having a floating sealing element with a surgical instrument inserted therethrough.
Figure 5B:
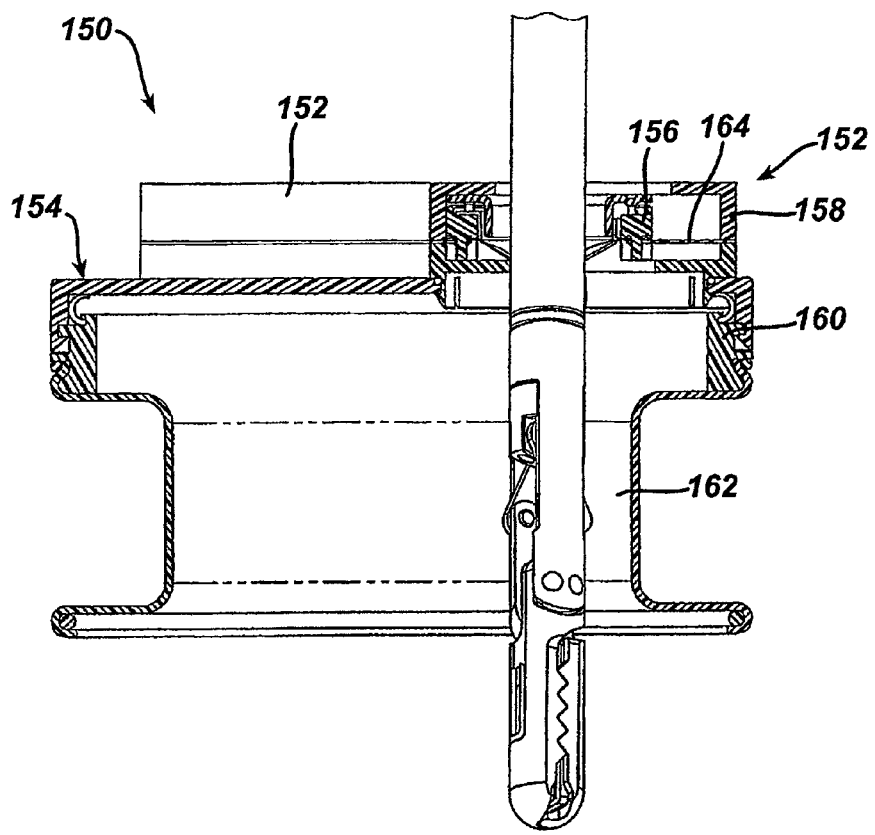
FIG. 5B is a cross-sectional view of the surgical access device of FIG. 5A showing the floating sealing element moved laterally.
Figure 5C:
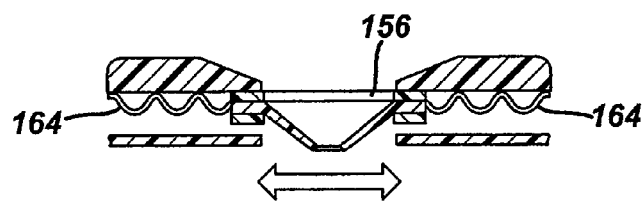
FIG. 5C is a cross-sectional view of one embodiment of a floating sealing element with a flexible membrane for allowing lateral movement.

In other embodiments such as those shown in FIGS. 5A-5C, a surgical access device 150 is provided having sealing ports 152 that are substantially parallel with a seal base 154. The sealing ports 152 can each have a port housing 158 that has a diameter larger than a diameter of a sealing element 156 disposed therein. The sealing element 156 can be positioned within the port housing 158 such that the sealing element 156 is movable within the larger diameter of the port housing 156. In one embodiment, shown most clearly in FIG. 5C, the sealing element 156 can be attached to a bellows-like structure or flexible membrane 164 that can stretch and bunch to allow the sealing element 156 to move laterally within the port housing 158. The sealing element 156 can thus be floating laterally relative to the port housing 158 and can move in multiple directions within a plane parallel to the seal base 154. Such a configuration allows a smaller incision through the body through which the retractor 162 extends, by allowing the sealing element 156 to move relative to the retractor 162 as needed. Exemplary movable and floating seal configurations are described in more detail in the following publications, all of which are incorporated herein by reference: U.S. Publication No. 2005/0070946, entitled "Reinforced Seal Assembly," filed on Sep. 17, 2004; U.S. Publication No. 2007/0255218, entitled "Pleated Trocar Seal," filed on Apr. 18, 2006; U.S. Pat. No. 5,385,553, entitled "Trocar with Floating Septum Seal," filed on Jun. 15, 1993; and U.S. Pat. No. 5,496,280, entitled "Trocar Valve Assembly," filed on May 19, 1994.

Figure 6A:
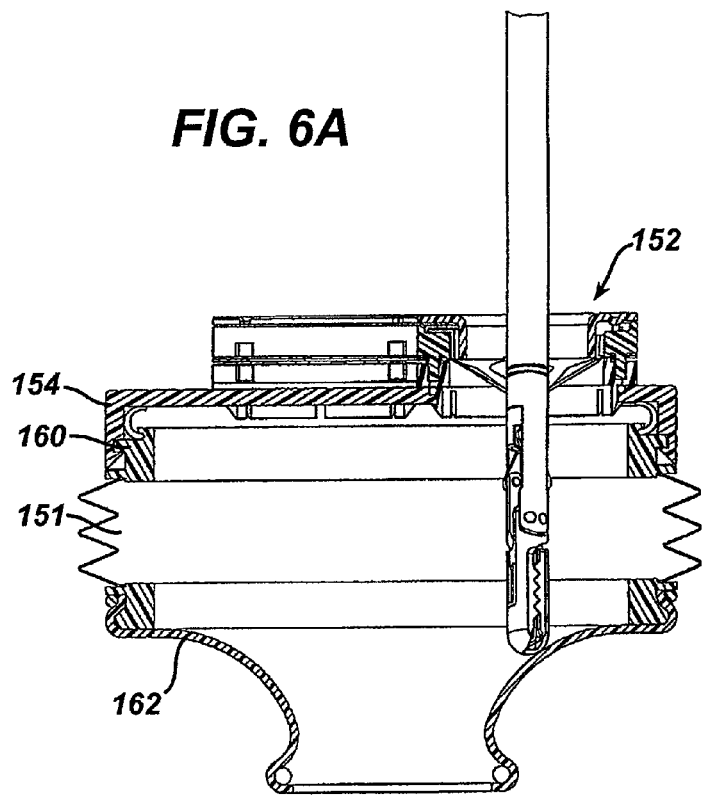
FIG. 6A is a cross-sectional view of one embodiment of a surgical access device having a bellows connector extending between a retractor and a housing.
Figure 6B:
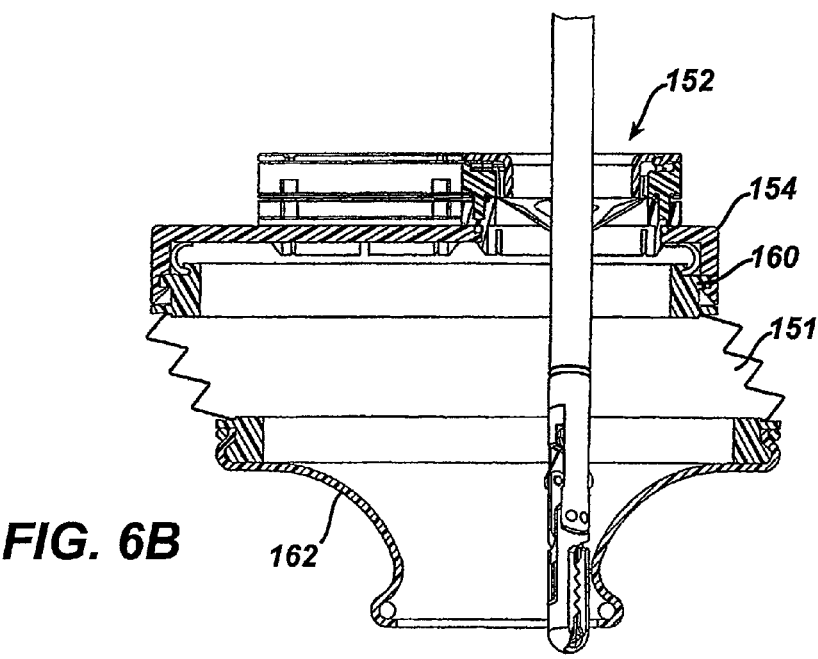
FIG. 6B is a cross-sectional view of the surgical access device embodiment of FIG. 6A showing the housing moved laterally relative to the retractor via the bellows connector.

The embodiments shown in FIGS. 5A and 5B can include a connector 151, as previously described with respect to FIGS. 3A and 3B, and as shown in FIGS. 6A and 6B. Such a configuration allows the housing 160 and the seal base 154 to be moved vertically via the connector 151 relative to the retractor 162 to change a height of the sealing ports 152 relative to the retractor 162. The housing 160 and the seal base 154 can also be moved laterally via the connector 151 to translate a position of the sealing ports 152 relative to the retractor 162, as shown, for example, in FIGS. 6A and 6B. As shown, the connector 151 can allow the sealing ports 152 to be moved laterally into alignment with the retractor 162 for easier insertion of surgical instruments. The housing 160 can further have limited rotational movement via the connector 151 to change the rotational position of the sealing ports 152. As will be appreciated by those skilled in the art, the housing can have any combination of vertical, lateral, and rotational movement via the connector 151 as needed in a particular application.

Figure 7A:
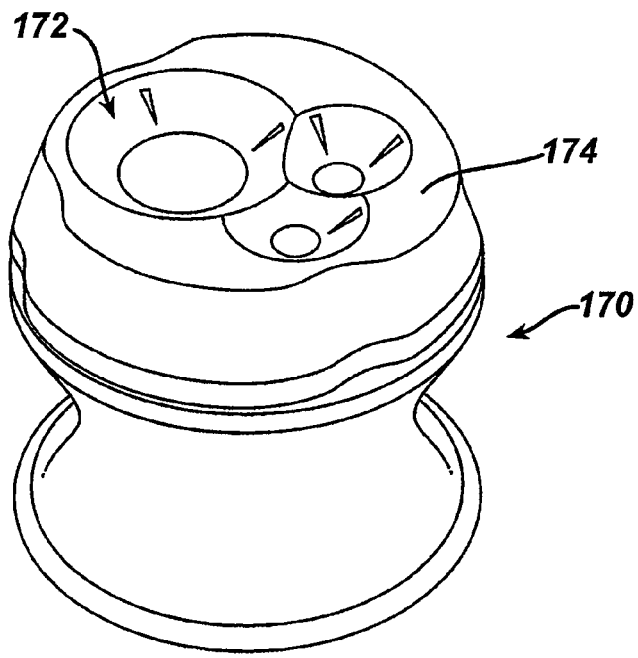
FIG. 7A is a perspective view of one embodiment of a surgical access device having a plurality of floating seals disposed therein.
Figure 7B:
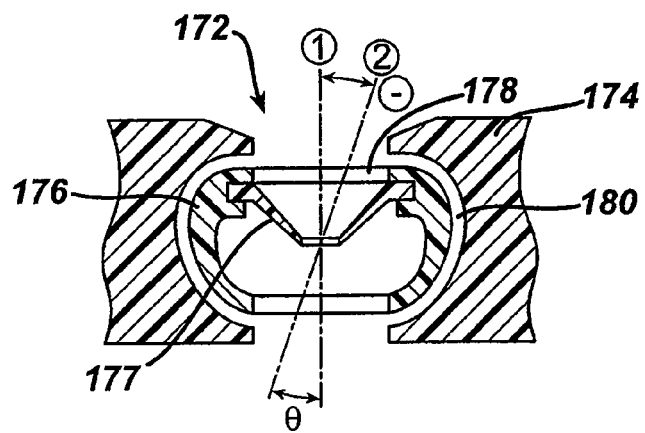
FIG. 7B is a cross-sectional view of a floating seal element capable of angular adjustment via one or more gimbals.
Figure 8A:
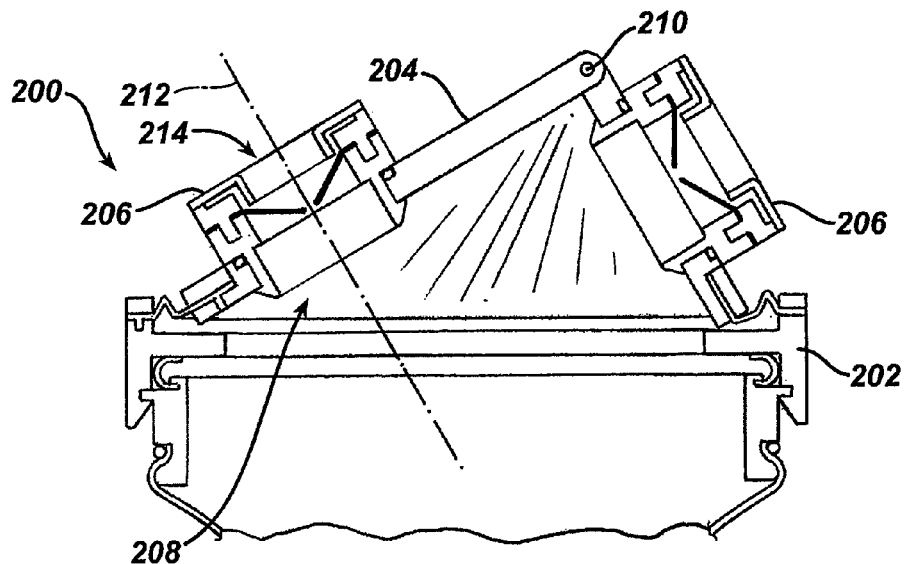
FIG. 8A is a cross-sectional view of one embodiment of a surgical access device having a hinged seal base.
Figure 8B:
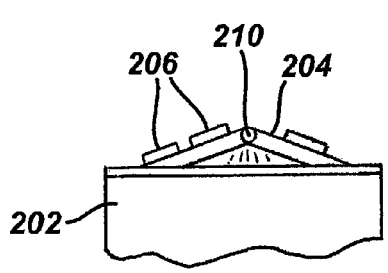
FIG. 8B is a cross-sectional view of the surgical access device embodiment of FIG. 8A.
Figure 8C:
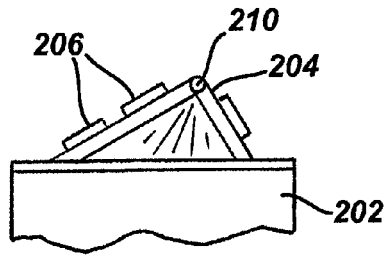
FIG. 8C is a cross-sectional view of the surgical access device embodiment of FIG. 8A showing the hinge moved.
Figure 8D:
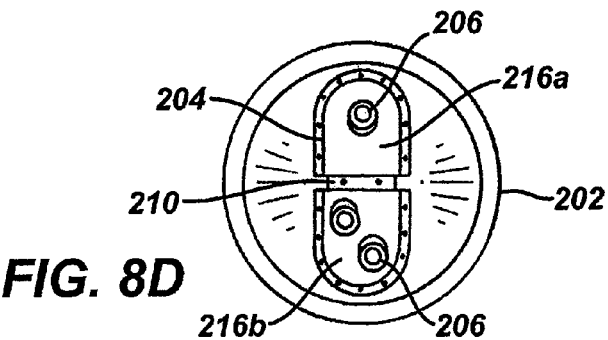
FIG. 8D is a top view of the surgical access device embodiment of FIG. 8A.

In another embodiment shown in FIGS. 7A and 7B, the surgical access device 170 can include a rotatable sealing port 172 that is rotatably seated in a port 180 formed in a seal base 174. The sealing port 172 can have one or more gimbal mechanisms 176 to allow a sealing element 178 to change its angular orientation with the port housing 180. The gimbal mechanism 176 can be, for example, a generally spherical member with flattened top and bottom portions and an opening extending therebetween with a seal element 177 extending thereacross. As shown, the gimbal 176, and the sealing element 178 can polyaxially rotate within the port housing 180 such that it is capable of multidirectional angular displacement. As shown in FIG. 7B, pivotal movement of the gimbal 176 and thus the sealing element 178 is effective to change the central longitudinal axis of the sealing element 178, allowing greater maneuverability for an instrument inserted therethrough.

In still another embodiment shown in FIGS. 8A-8D, a surgical access device 200 is provided having a housing 202 with a hinged seal base 204. One or more sealing ports 206 can extend through the hinged seal base 204 and can be configured to receive surgical instruments therethrough. The hinged seal base 204 can be selectively movable between various angular configurations relative to a top opening 208 of the housing 202 via a hinge 210 positioned within the seal base 204. The hinge can be located anywhere on the seal base 204, and any number of ports can be positioned in one or both sides of the hinge to allow angular adjustment of the ports. In lower profile configurations, the sealing ports 206 can have a central axis 212 that is substantially parallel to the central axis of the top opening 208 of the housing 202. The sealing ports 206 can be moved into higher profile configurations, such as that shown in FIGS. 8A-8C, in which the central axis 212 of the sealing ports 206 forms an angle relative to the central axis of the opening 208 in the housing 202. In this way, the angular orientation of the sealing ports 206 can be changed and adjusted by simply changing the position of the hinged seal base 204. It will be appreciated that the hinged seal base 204 can be locked or maintained at any position between the low profile configuration and high profile configurations as needed. A latch, switch, or other locking mechanism known in the art can be used.

In some embodiments, as will be appreciated by those skilled in the art, any number of sealing ports 206 can be disposed in each section 216a, 216b of the hinged seal base 204. In addition, there can be one or more hinges 204 formed in the seal base 204 to allow for multiple movable surfaces. In one embodiment, a flexible membrane or other stretchable and/or flexible material can be used to connect the hinged seal base 204 with the housing 202 to ensure that a gas and liquid tight seal is maintained while allowing the hinged seal base 204 to move between low and high profile configurations. A person skilled in the art will appreciate the various other techniques can be used to allow the hinged seal base 204 to move relative to the housing 202 while maintaining a seal therebetween.

Figure 9A:
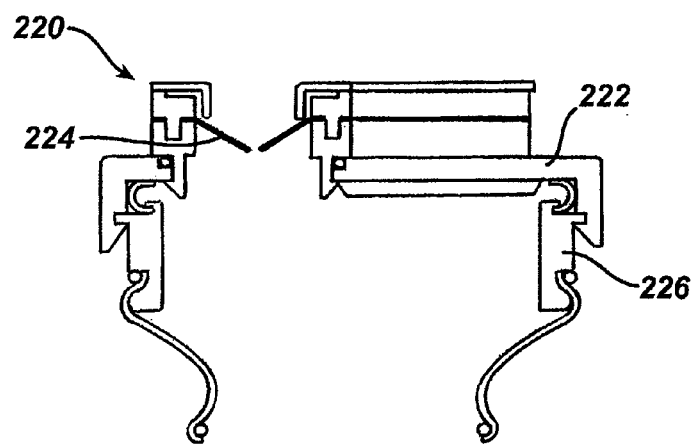
FIG. 9A is a cross-sectional view of another embodiment of a surgical access device having a raised sealing element formed in a seal base.
Figure 9B:
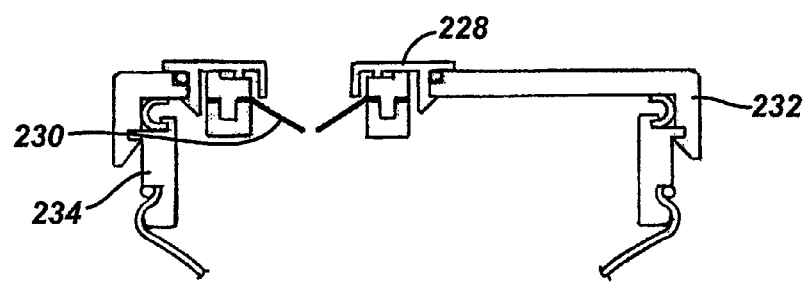
FIG. 9B is a cross-sectional view of one embodiment of a surgical access device having a sealing element that is flush with a seal base.
Figure 9C:
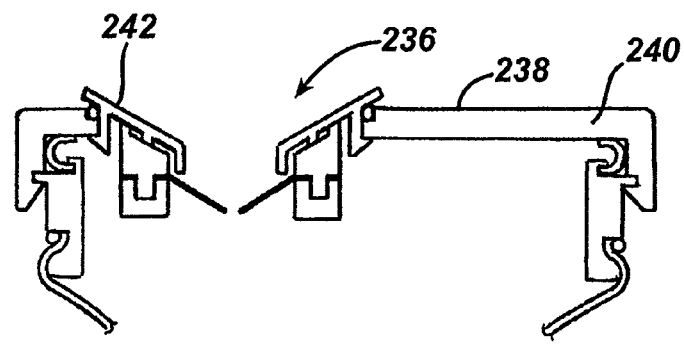
FIG. 9C is a cross-sectional view of one embodiment of a surgical access device having a sealing element that is recessed in a seal base.

Any and all of the access ports, sealing ports, and/or sealing elements described herein can also be positioned at various vertical orientations within a seal base and housing of a surgical access device. For example, as shown in FIG. 9A, a raised sealing port 220 is positioned above a seal base 222 such that a surgical instrument inserted therethrough will travel through a sealing element 224 before traveling through the seal base 222 and entering a housing 226. In another embodiment shown in FIG. 9B, a sealing port 228 is flush or parallel with the a seal base 232 such that a surgical instrument inserted therethrough enters a sealing element 230 concurrently with entering the seal base 232. In a further embodiment shown in FIG. 9C, a sealing port 236 can be in a recessed position below a proximal surface 238 of a seal base 240. Angled guides 242 can direct a surgical instrument into the recessed sealing port 236 to facilitate accurate insertion of the instrument.

Figure 9D:
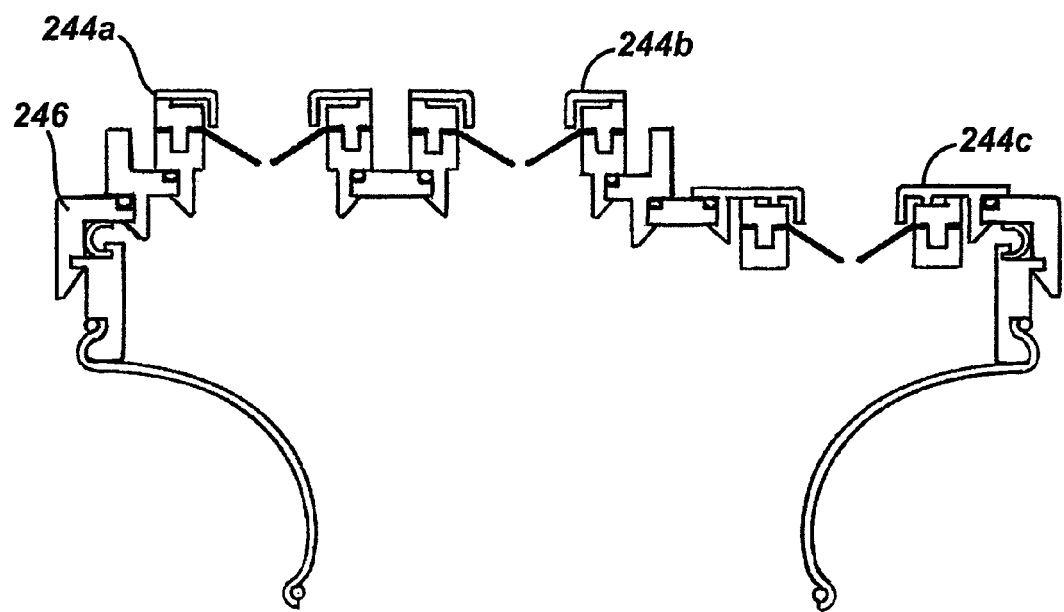
FIG. 9D is a cross-sectional view of another embodiment of a surgical access device having sealing elements positioned at different levels within the seal base.

In addition, as shown in FIG. 9D, multiple sealing ports 244a, 244b, 244c can also be configured at various heights relative to a seal base 246. For example, the proximal surface of sealing ports 244a and 244b, as well as the sealing elements disposed therein, can be positioned substantially coplanar with one another at the same height relative to the seal base 246, while the proximal surface of sealing port 244c, as well as the sealing element therein, is positioned lower than sealing ports 244a and 244b. Using sealing ports and sealing elements that are of different heights and/or are off-plane from each other can allow for the longitudinal axis of the sealing port, and subsequently the instrumentation used, to be closer together, thereby allowing for a smaller incision or use in a smaller opening in tissue. In one embodiment, the off-plane sealing ports can allow for the use of larger sealing ports and/or sealing elements within the same space by overlapping the edges of the sealing ports and/or sealing elements because they can be on different planes. In addition, during retraction of target tissue, the off-plane sealing ports can provide for custom angles depending on the instrumentation intended to be used with the sealing port. In other embodiments, instead of being off-plane, any one or all of the sealing ports can have flattened side walls to enable the sealing ports to be positioned closer together within the seal base. As will be appreciated by those skilled in the art, exemplary surgical access devices can have seal ports at any number of vertical orientations, including all sealing ports being at a different vertical heights. In addition, any number of the sealing ports can be spaced and positioned laterally within a seal base in any configuration as needed. The sealing ports can also extend in a plane transverse to a plane of the base, as previously discussed.

In another exemplary embodiment shown in FIGS. 10A-10D, a proximal portion 250 of a surgical access device is provided having a cylindrically shaped seal base 252 mated with a housing 266 and having three recessed access or sealing ports 254a, 254b, and 254c extending therethrough. Two of the sealing ports 242a, 254b can have a first diameter D1, and the third sealing port 254c can have a second diameter D2, which can be larger than the first diameter D1. In certain exemplary embodiments, the first diameter D1 is about 3 mm and the second diameter D2 is about 5 mm. A person skilled in the art will appreciate that there can be any number of sealing ports disposed within the seal base 252 and the sealing ports can have any combination of diameters as needed. As shown, the sealing ports 254a, 254b, 254c can be recessed into the seal base 252 so that a proximal surface 256 of the seal base 252 is substantially flat. Guides 258 can direct a surgical instrument into sealing elements, for example into an instrument seal 260 and a channel seal 262, disposed within the sealing ports 254a, 254b, 254c.

Figure 10A:
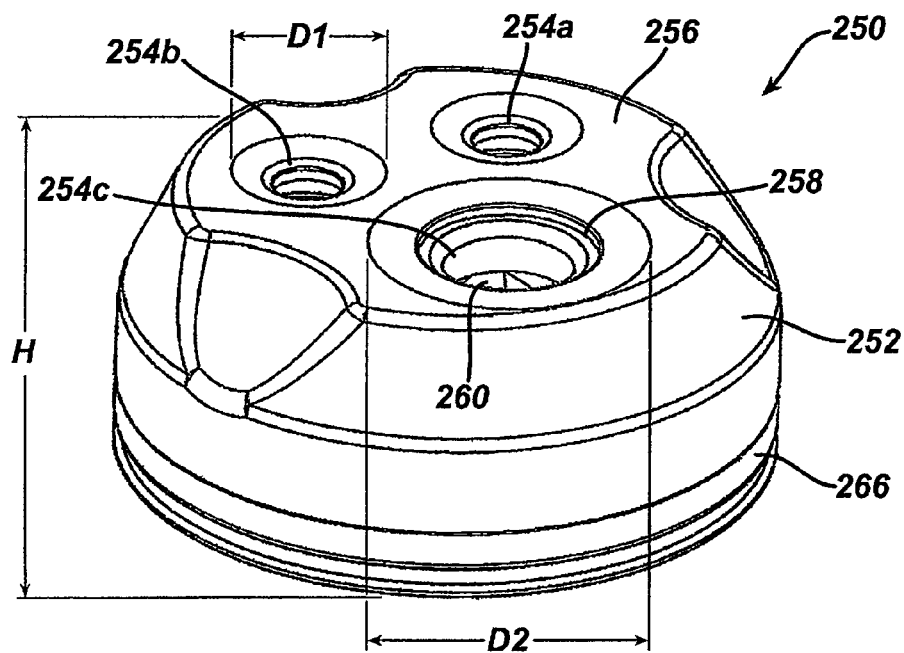
FIG. 10A is a perspective view of one embodiment of a seal base for a surgical access device having recessed sealing elements disposed therein.
Figure 10B:
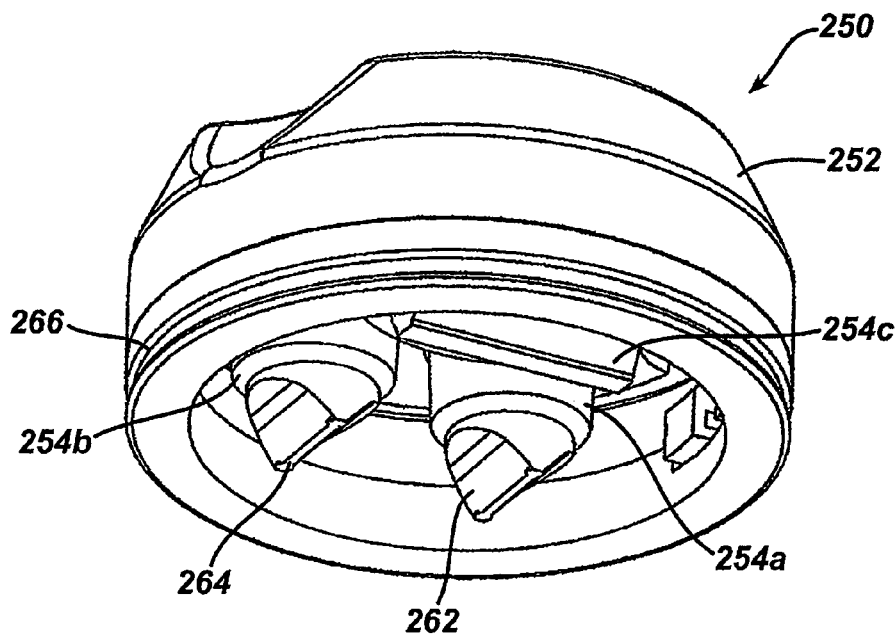
FIG. 10B is another perspective view of the seal base embodiment of FIG. 10A showing recessed channel sealing elements.
Figure 10C:
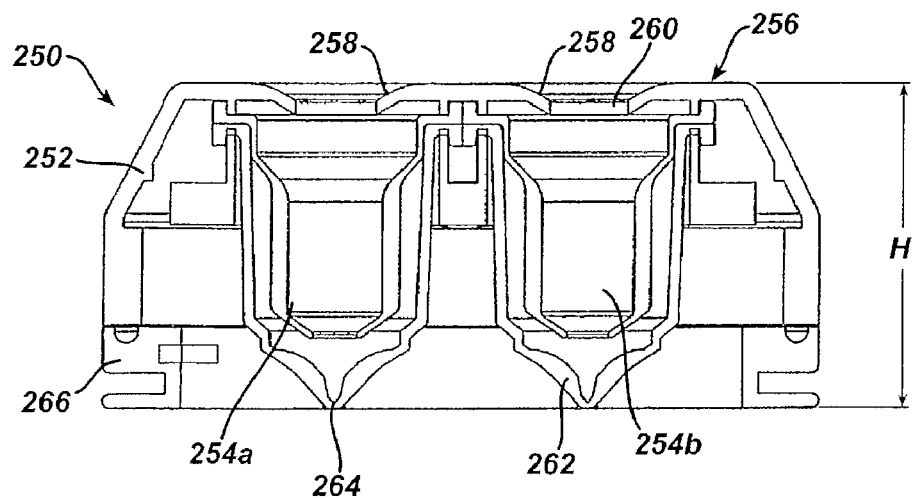
FIG. 10C is a cross-sectional view of the seal base embodiment of FIG. 10A.
Figure 10D:
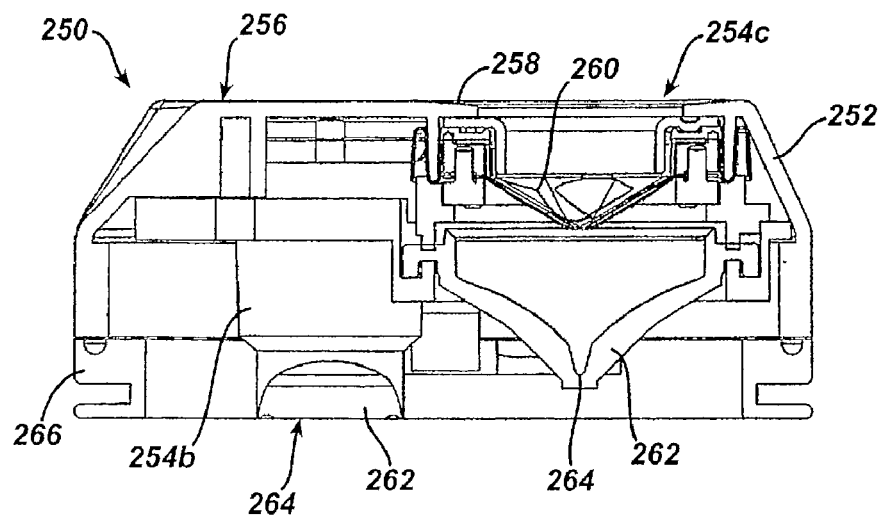
FIG. 10D is another cross-sectional view of the seal base embodiment of FIG. 10A.

The seal base 252 and/or the housing 266 can have a height H to accommodate a full length of the channel seals 262 to prevent channel seal openings 264 from coming into contact with a retractor (not shown) extending from the housing 266. This configuration can prevent retractor sidewalls from contacting the channel seal openings 264 and causing them to open when the seal base 252 and the housing 266 is moved relative to the retractor. In other embodiments, the seal base 252 and the housing 266 can have a total height H less than a longitudinal length of the channel seals 262. In such a configuration, each channel seal opening 264 can be oriented to minimize contact with the retractor. For example, each seal opening 264 can be aligned tangential to a circumference of the seal base 252, the housing 266, and a retractor extending from the housing 266 as shown in FIG. 10B. In other words, the opening can extend in a direction that is substantially parallel to a circumference of the housing 266, and not transverse to the housing 266. Such an alignment can prevent the channel seal opening 264 from being pushed open by a retractor sidewall when the seal base 252 and the housing 266 is moved relative to the retractor. A person skilled in the art will appreciate that, while duckbill seals are shown, any sealing elements known in the art can be aligned in such a way, including non-linear sealing elements, for example sealing elements with an S-shaped opening.

Figure 11A:
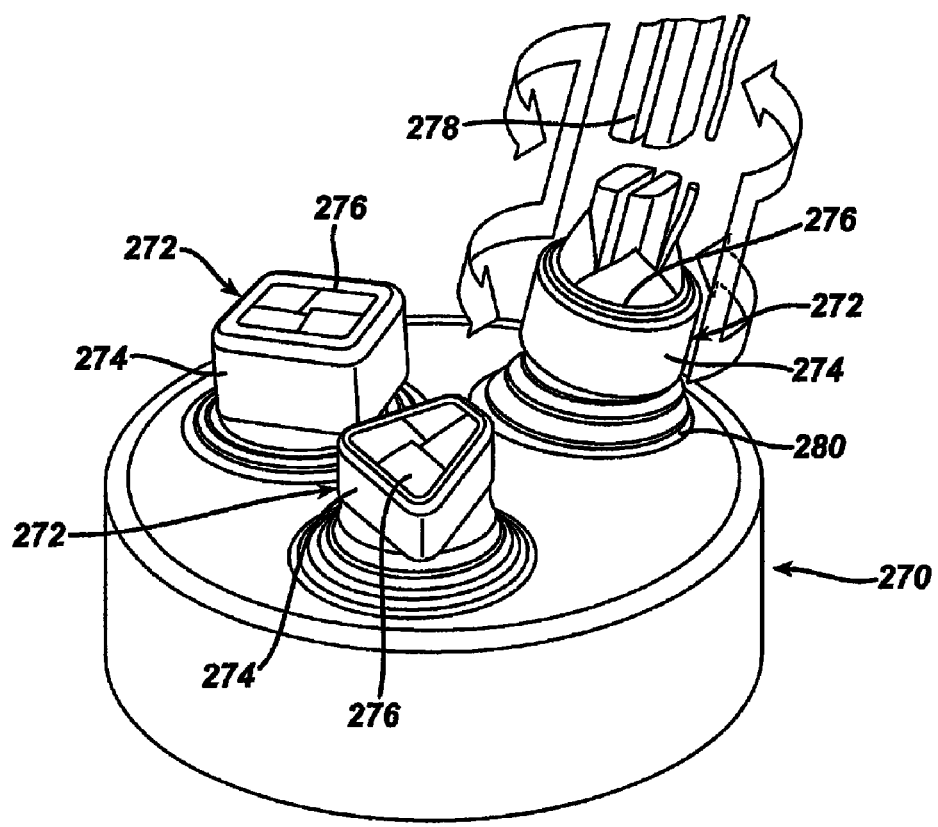
FIG. 11A is a perspective view of one embodiment of a seal base for use with a surgical access device showing sealing ports having non-circular apertures.

In another embodiment shown in FIG. 11A, a seal base 270 is provided having a plurality of access or sealing ports 272 extending therethrough. One or more of the sealing ports 272 can have a port housing 274 and/or a sealing element 276 with a non-circular shaped opening to receive a surgical instrument 278 having a non-circular cross-section. The non-circular shaped sealing ports 272 can have any shape known in the art, including but not limited to oval, triangular, quadrilaterals, polygons, etc. Each port housing 274 and/or sealing element 276 can be rotatable relative to the seal base 270 so that as the non-circular shaft of a surgical instrument 278 is inserted therethrough, the sealing port 272 can rotate to orient itself in alignment with the cross-sectional shape of the surgical instrument 278. In one embodiment, the sealing ports 272 can be attached to the seal base 270 using a bellows connector or other flexible member 280 to allow the sealing port 272 to move vertically and/or laterally with respect to the seal base 270.

Figure 11B:
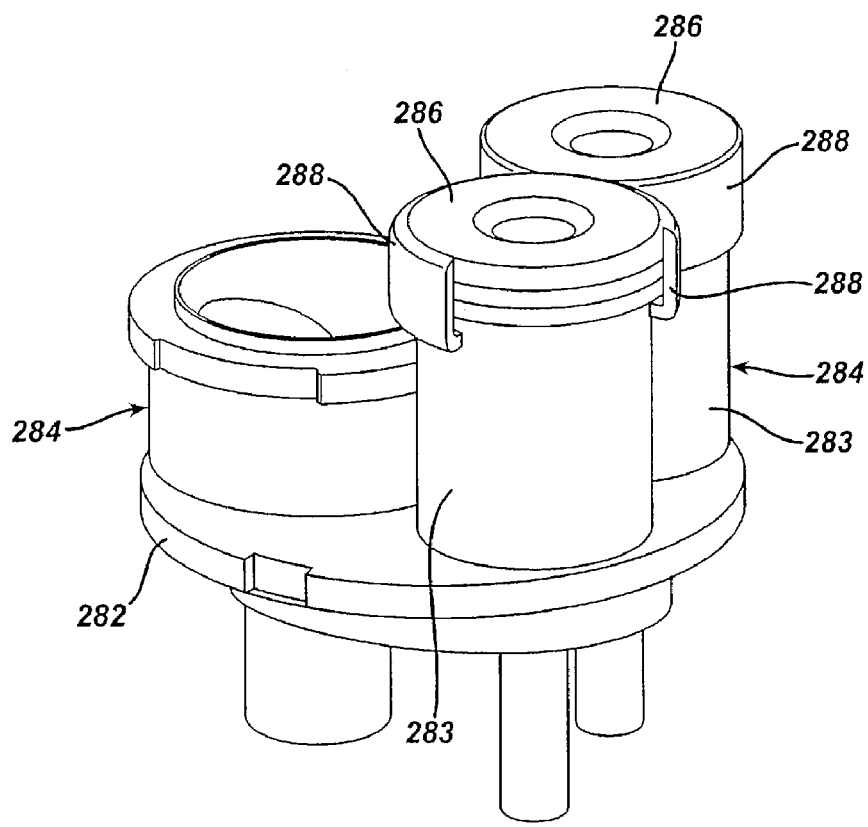
FIG. 11B is a perspective view of one embodiments of a seal base for use with a surgical access device showing flexible sealing ports.

In another embodiment shown in FIG. 11B, a seal base 282 is provided having a plurality of sealing ports 284 extending therethrough. Each of the sealing ports 284 can have sealing elements 286 disposed therein. The sealing ports 284 can have a port housing 283 that is flexible to allow the port housing 283 to move vertically, laterally, and angularly relative to the seal base 282. In some embodiments, at least a portion of the sealing ports 284 and/or the port housing 283 can be corrugated and/or can be formed of a bellows or other flexible material or flexible mechanism. Each of the sealing ports 284 can also have a release mechanism, such as a C-clamp 288, that allows the sealing element 286 or other component of the sealing port 284 to be removed to allow specimens or other objects to be therethrough. The port housings 283 can also vary in height as shown. A person skilled in the art will appreciate the various flexible portions that can be used to allow the port housing 286 to move relative to the seal base 282.

Figure 12A:
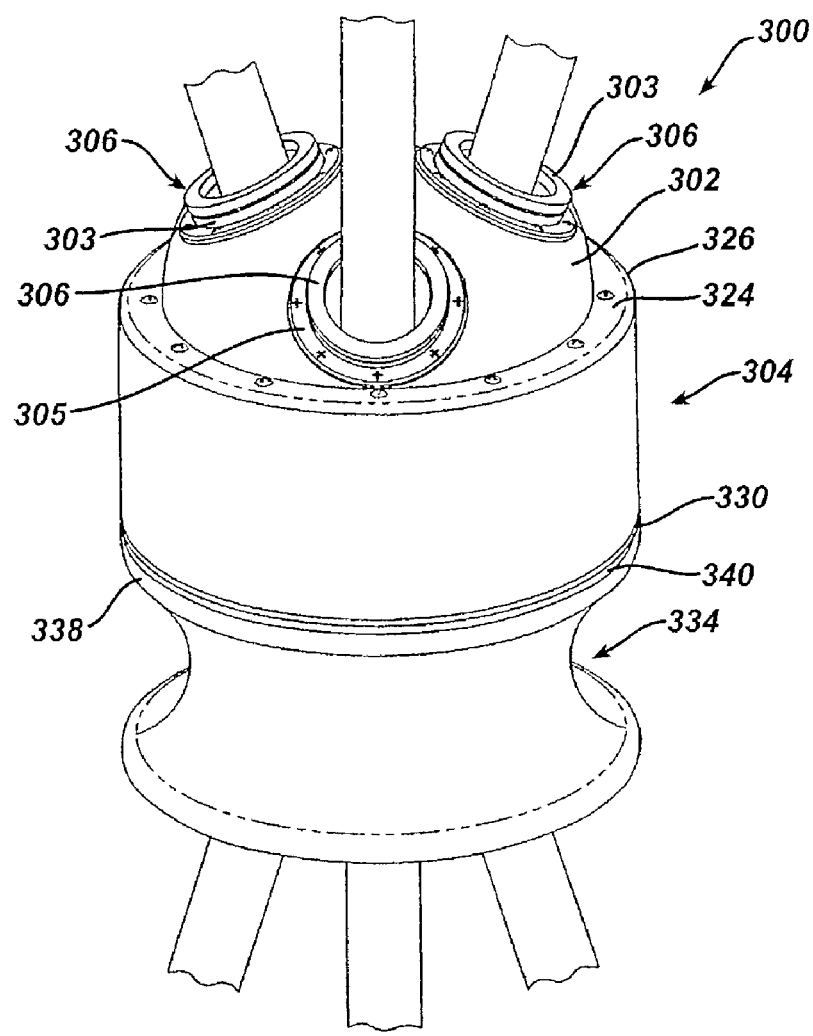
FIG. 12A is a perspective view of one embodiment of a surgical access device having a flexible seal base with sealing ports formed therethrough.
Figure 12B:
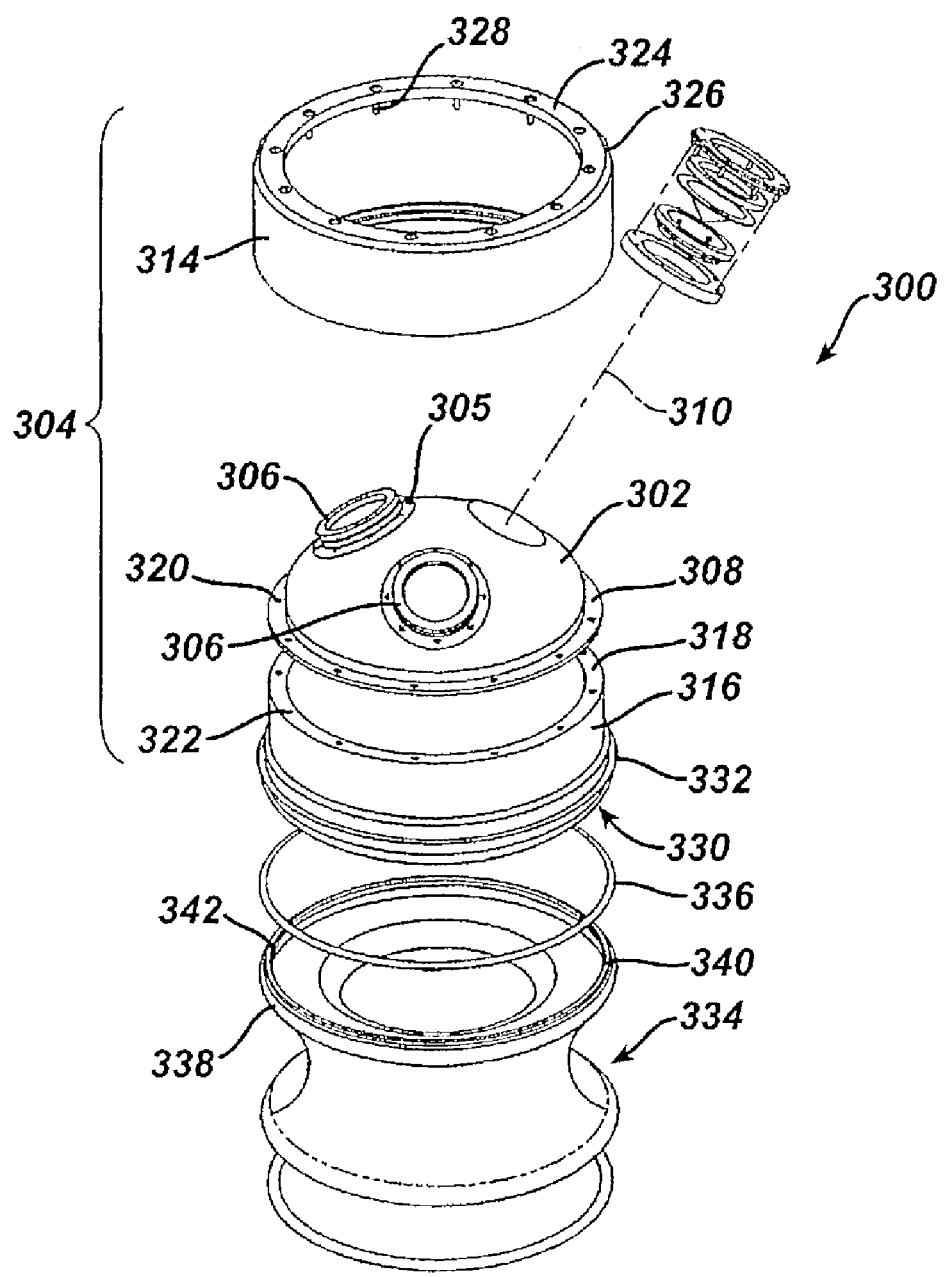
FIG. 12B is an exploded view of the surgical access device of FIG. 12A.
Figure 12C:
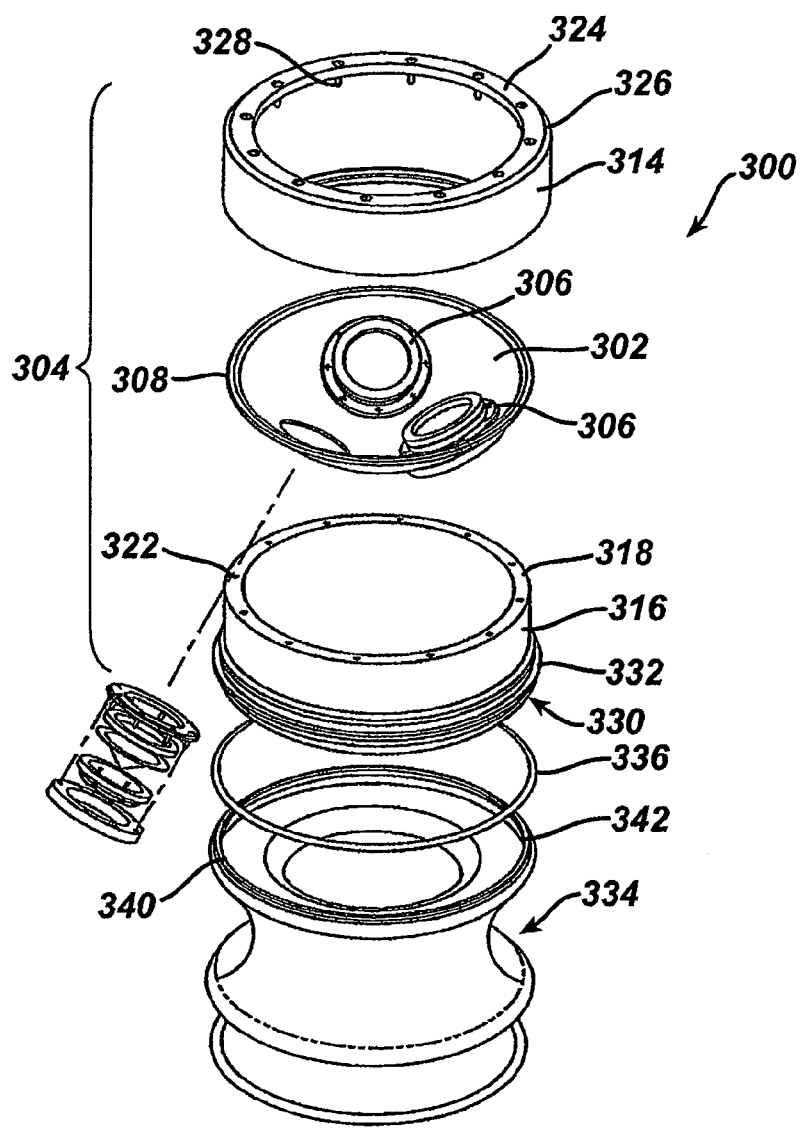
FIG. 12C is an exploded view of the surgical access device of FIG. 12A showing the flexible seal base in a concave configuration.
Figure 12D:
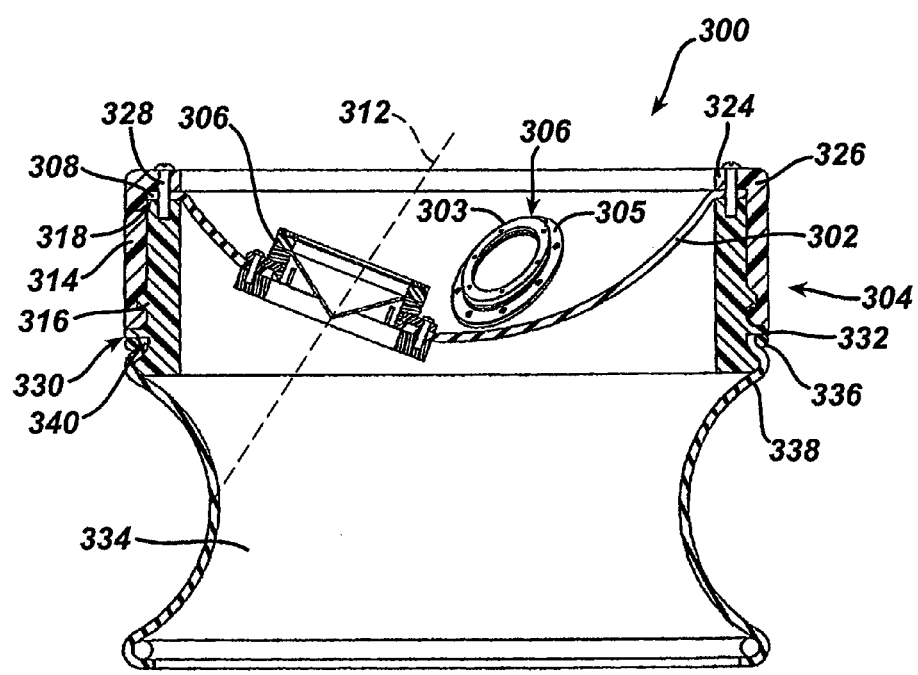
FIG. 12D is a cross-sectional view of the surgical access device of FIG. 12A showing the flexible seal base in a concave configuration.

In another embodiment shown in FIGS. 12A-12D, a surgical access device 300 is provided having a flexible seal base 302 and a housing 304. The flexible seal base 302 can have one or more access or sealing ports 306 formed therethrough for receiving a surgical instrument. The flexible seal base 302 can have any shape, but in the illustrated embodiment is generally dome shaped with a flange 308 extending around a distal circumference thereof that is configured to mate with the housing 304 as will be described below. As a result, the flexible seal base 302 has a concave configuration, in which it extends proximally from the housing 304, as shown in FIGS. 12A and 12B, and a convex configuration in which it extends distally into the housing 304, as shown in FIGS. 12C and 12D. The flexible seal base 302 can be selectively moved between the convex and concave configurations as needed to reorient one or more of the sealing ports 306.

The sealing ports 306 can be formed or disposed in the flexible base 302 using various techniques. In the illustrated embodiment, each seal port 306 is in the form of a rigid ring-shaped member that supports the sealing element 303, which can likewise include a rigid ring-shaped structure 305. The ring 305 around the seal elements 303 can be fixedly or movably seated within the rigid ring 305 that forms the seal port 306 in the flexible base 302.

In one embodiment, when the flexible seal base 302 is in the convex configuration, the sealing ports 306 can have first central axes 310 such that a surgical instrument is inserted at a specified angle or orientation. When the flexible seal base 302 is moved toward or into the concave configuration, the sealing ports 306 can transition toward or into to second central axes 312 such that a surgical instrument is inserted at a different angle or orientation than in the convex configuration. When the flexible seal base 302 is in the convex configuration, the central axes of the sealing ports 306 are generally oriented in a distal direction toward a center of the flexible seal base 302 and the housing 304. When the flexible seal base 302 is moved into a concave configuration, the central axes of the sealing ports 306 can be generally directed in a distal direction outward from the center of the flexible seal base 302 and housing 304. As shown, the sealing ports 306 can be generally situated proximally to the housing 304 when the flexible seal base 302 is in the convex configuration. In the concave configuration, the sealing ports 306 can generally extend into the housing 304.

In one embodiment, the housing 304 that supports the base 302 can be substantially rigid, although it will be appreciated that it can be flexible as needed in a specific application, and it can be generally cylindrical or tubular in shape. The housing 304 can have an outer component 314 and an inner component 316 concentrically positioned and nested together. The flange 308 of the flexible seal base 302 can be positioned on a proximal rim 318 of the inner component 316 and oriented such that holes 320 formed in the flange 308 are aligned with corresponding holes 322 formed in the proximal rim 318. The outer component 314 can have a flange 324 on a proximal most rim 326 that extends toward a center of the outer component 314. The flange 324 can have posts 328 extending distally therefrom configured to mate the flexible seal base 302 and the inner component 316. The outer component 314 can be positioned over and around the inner component 316 and oriented such that the posts 328 will engage and extend through the aligned holes 320, 322 of the flexible seal base flange 308 and the inner component rim 318. In this way, the outer component 314 can secure the flexible seal base flange 308 between the two concentric components 314, 316. A person skilled in the art will appreciate the variety of other mating and securing mechanisms can be used to secure the rim of the flexible seal base 302 to the housing 304.

In one embodiment, a distal portion 330 of the inner component 316 of the housing 304 can have threads 332 formed around an exterior thereof for mating with a retractor 334. An o-ring 336 can be positioned between the distal portion 330 of the inner component 316 and a proximal flange 338 of the retractor 334 to ensure a gas and liquid tight seal between the two. The proximal flange 338 of the retractor 334 can have a circumferential lip 340 extending proximally that can have threads 342 extending around an interior circumference thereof. The distal threaded portion 330 of the inner component 316 can be threaded into the lip 340 of the retractor 334, thereby securing the housing 302 with the retractor 334.

Figure 13A:
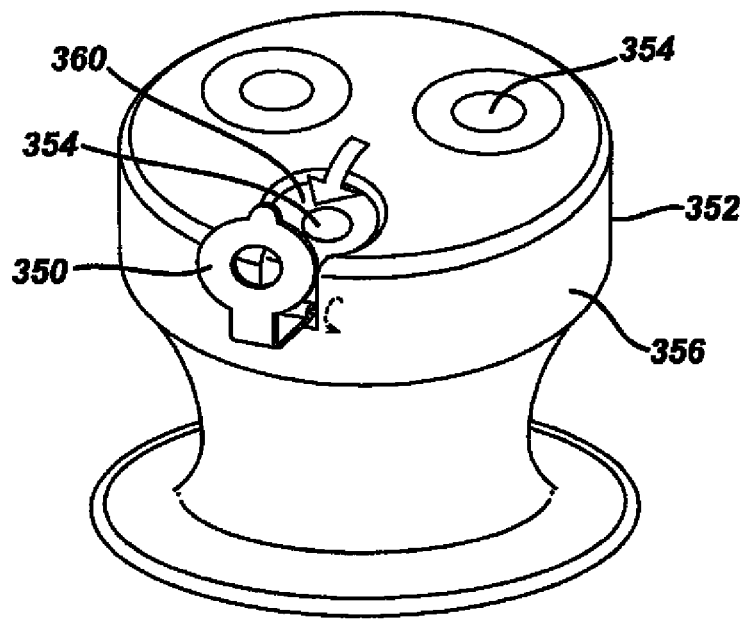
FIG. 13A is a perspective view of one embodiment of a surgical access device having an adapter for changing an effective sealing port diameter.
Figure 13B:
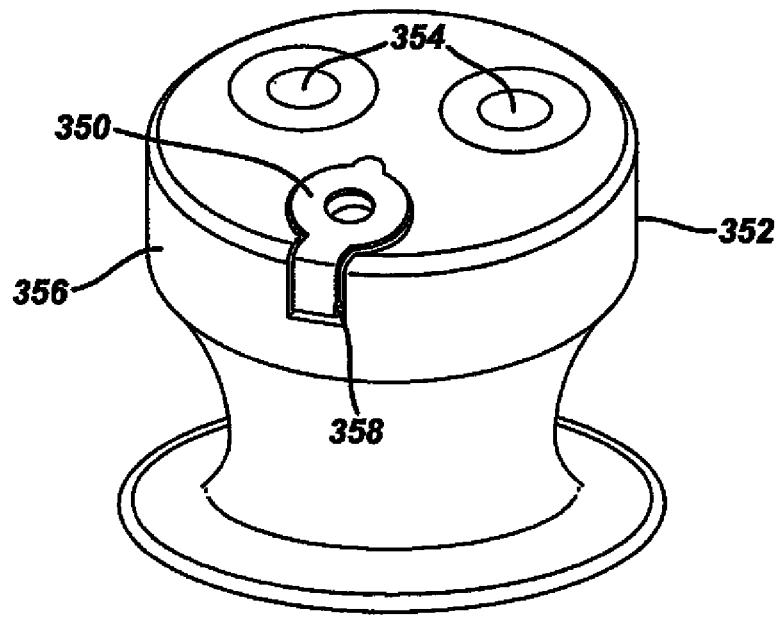
FIG. 13B is a perspective view of the surgical access device of FIG. 13A.

In other exemplary embodiments, any and all of the surgical access device embodiments discussed herein, as well as in any combinations thereof, can have an adapter removably matable to at least one of the sealing ports to change a size, shape, or orientation of the sealing port without loss of pneumoperitoneum. In one embodiment, shown in FIGS. 13A and 13B, the adapter 350 can be rotatably or pivotably attached to a portion of a seal base 352, and it can be selectively positionable adjacent to a sealing port 354 to change a feature of the sealing port 354. In particular, in the embodiment shown in FIGS. 13A and 13B, the adapter 350 is a sizing adapter to change an effective diameter of the sealing port 354 disposed within the seal base 352. The adapter 350 can be pivotably attached to a portion of an outer circumference 356 of the seal base 350 such that it can move between open and closed configurations. In an open configuration, the adapter 350 can be positioned away from an opening of the sealing port 354, as shown in FIG. 13A. In the closed configuration, the adapter 350 can be pivoted or rotated via a hinge 358 such that it is positioned over an opening 360 of the sealing port 354 to thereby change an effective diameter of the sealing port 354. For example, in the open configuration, the sealing port 354 can receive a surgical instrument having a 12 mm diameter. In the closed configuration, the adapter 350 can allow the sealing port 354 to receive a surgical instrument with a 5 mm diameter. A person skill in the art will appreciate that any size adjustments can be made with such an adapter 350 as needed.

In other embodiments, an adapter can change an effective shape of a sealing port. For example, the sealing port can have a circular shape to receive an instrument with a circular cross-section when the adapter is in an open configuration. In the closed configuration, the adapter can allow the sealing port to receive a surgical instrument having a non-circular cross-section such as a triangle, oval, quadrilaterals, and/or other polygons. In addition, the adapter can also allow an effective orientation change of a sealing port. As will be appreciated by those skilled in the art, a shape and size change can be combined into a single adapter as needed.

As will also be appreciated by those skilled in the art, any and all of the seal base and housing embodiments disclosed herein can be interchangeable with one another as needed. For example, a kit could include multiple housings and seal bases with one or more retractors. Each seal base and housing combination can have different sized, shaped, and/or angled sealing ports extending therethrough so that a surgeon can actively change housings and seal bases as needed. A release mechanism, such as those described in detail below, can be used to releasably attach the various seal bases and housings to a retractor.

A person skilled in the art will also appreciate that the various features disclosed herein can likewise be incorporated into a single port access device. FIGS. 14A-14D illustrate another embodiment of a surgical access device in the form of a trocar assembly 370 having a housing 372 and a flexible cannula 374 extending therefrom. The housing 372 can have a sealing element 376 disposed therein that is rotatable with respect to the housing 372 to allow rotation and adjustment of a device inserted within the sealing element 376 without requiring rotation of the trocar housing 372 and the flexible cannula 374. For example, if an endoscope is inserted through the trocar assembly 370, the sealing element 376 can rotate with the endoscope and independently of the housing 372 and the flexible cannula 374 to allow adjustment in what is being viewed by the endoscope.

Figure 14A:
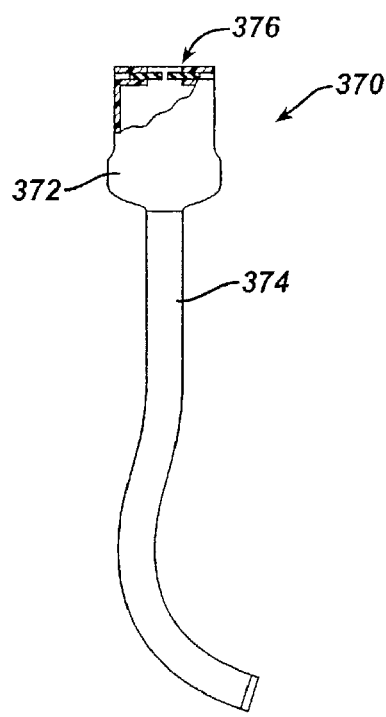
FIG. 14A is a side view of an embodiment of a surgical access device in the form of a trocar assembly having a rotatable sealing element.
Figure 14B:
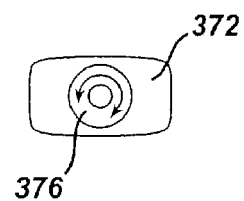
FIG. 14B is a top view of the surgical access device of FIG. 14A showing the rotatable sealing element.
Figure 14C:
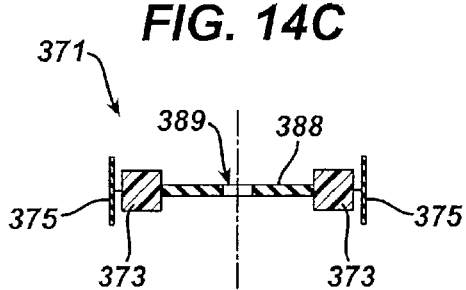
FIG. 14C is a cross-sectional view of one embodiment of a rotatable sealing element for use in the surgical access device of FIG. 14A.

In one embodiment shown in FIG. 14C, a rotatable seal 371 is provided having an annular disc 373 positioned within an elastic outer ring 375. The annular disc 373 can be flexible or rigid and a sealing element 388 can be disposed therein with an opening 389 formed therethrough for receiving a surgical instrument. The annular disc 373 can be mated to the elastic outer ring 375 by any mating mechanism known in the art, such as a flange extending between the annular disc 373 and the outer ring 375. The elastic outer ring 375 can be positioned within a groove formed in the housing 372 of the trocar assembly 370, thereby allowing the rotatable seal 371 to rotate relative to the housing while maintaining a seal around a surgical instrument inserted therethrough.

Figure 14D:
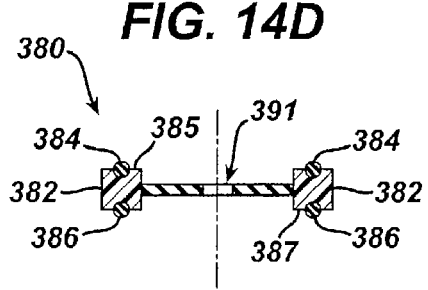
FIG. 14D is a cross-sectional view of another embodiment of a rotatable sealing element for use in the surgical access device of FIG. 14A.

In another embodiment shown in FIG. 14D, a rotatable seal 380 is provided having an annular disc 382 that can be positioned within the housing 372 of the trocar assembly 370. The annular disc can have a sealing element 390 positioned therein with an opening 391 formed therethrough for receiving a surgical instrument. The annular disc 382 can have a top o-ring 384 and a bottom o-ring 386 disposed on top and bottom surfaces 385, 387 thereof for forming a seal between the annular disc 382 and the housing 372. The annular disc 382 can rotate relative to the housing 372, while the o-rings 384, 386 maintain a seal therebetween. A person skilled in the art will appreciate that a variety of mechanisms can be used to create a rotatable seal within the housing 372 of the trocar assembly 370.

The trocar assembly 370 can include other features as well, such as a cable or other steering mechanism to provide steering control over the flexible cannula 374. In this case, the flexible cannula 374 and the instrument inserted within the sealing element 376 through the flexible cannula 374 can be independently movable and controllable as needed.

As surgical instruments are inserted through the surgical access device embodiments described herein, a risk can exist that a particularly sharp instrument may tear or puncture a portion of the retractor or nearby tissue. Accordingly, in any and all of the embodiments described herein, a safety shield can optionally be included to reduce the risk of tearing or puncture by a surgical instrument. In general the shield can be of a material that is relatively smooth to allow ease of passage of instruments, but resistant to tearing and puncture. For example, the shield can formed of silicone, urethane, thermoplastic elastomer, rubber, polyolefins, polyesters, nylons, fluoropolymers, and any other suitable materials known in the art. The shield can generally provide a liner for a retractor or tissue and can be detachable from a surgical access device so it can be used as needed in a particular procedure.

Figure 15A:
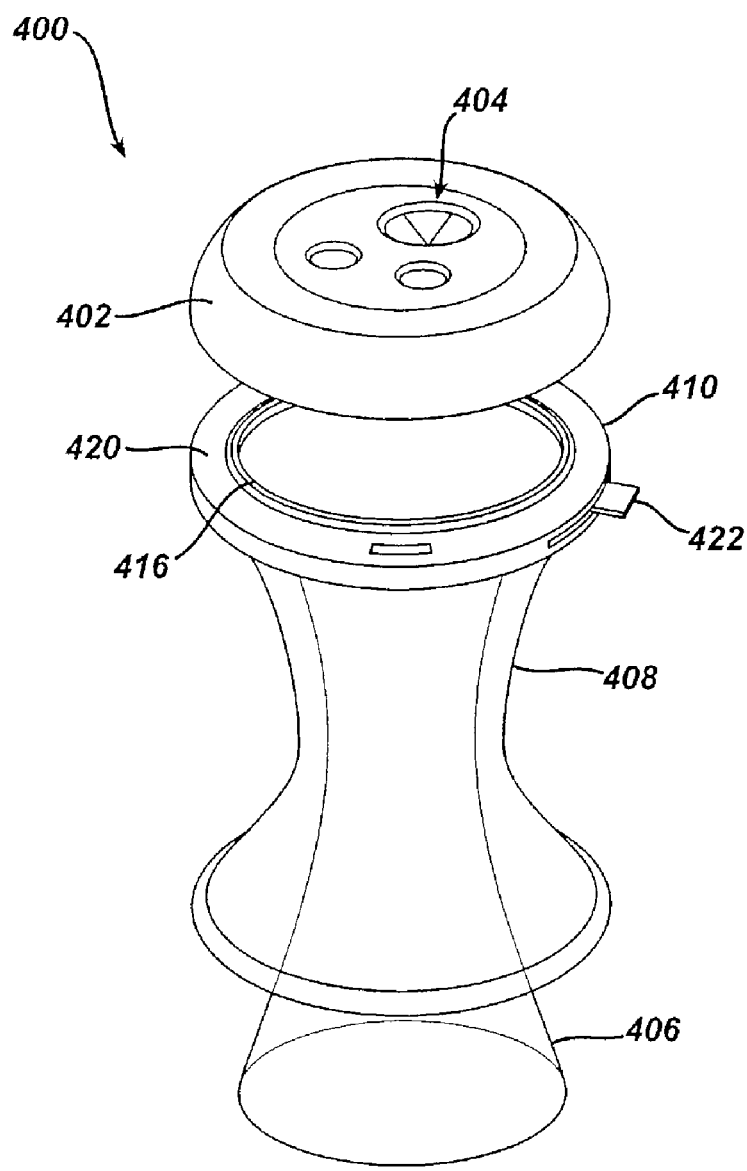
FIG. 15A is a perspective view of one embodiment of a surgical access device having a shield extending through a retractor.
Figure 15B:
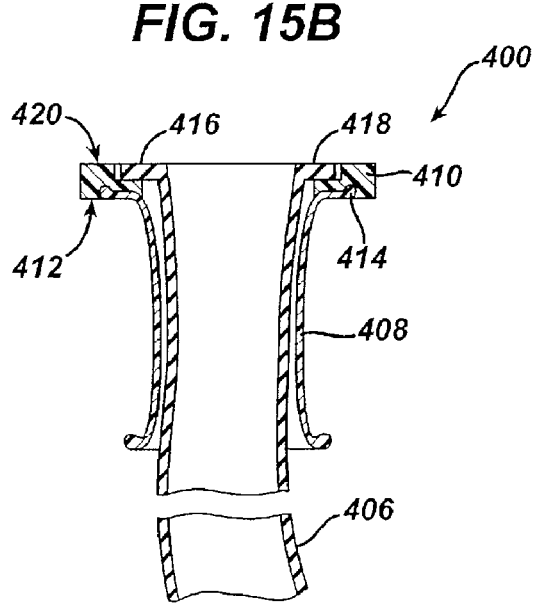
FIG. 15B is a cross-sectional view of the surgical access device of FIG. 15A.
Figure 15C:
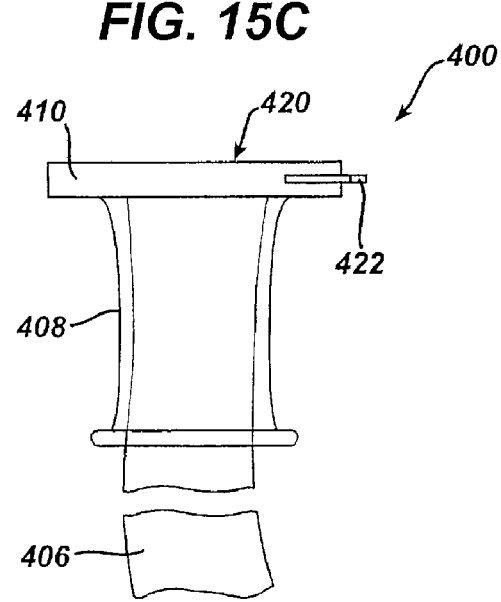
FIG. 15C is a side view of the surgical access device of FIG. 15A.

In one exemplary embodiment shown in FIGS. 15A-15C, a surgical access device 400 is provided having a seal base 402 with a plurality of sealing ports 404 extending therethrough. The surgical access device 400 can also include a shield 406 and a retractor 408. As shown, the shield 406 can extend through the retractor 408 to thereby provide a protective lining as surgical instruments are inserted through the device. The shield 406 can have a length corresponding to a length of the retractor 408, but can also have a length considerably longer than the length of the retractor depending on a specific application. The retractor 408 and the shield 406 can be mated to a housing 410. For example, the retractor 408 can have a proximal flange 414 that can be mated to a distal portion 412 of the housing 410. Any mating mechanism known in the art can be used, for example, adhesive, screws, press fit, etc. The shield 406 can have a proximal flange 416 that can be seated within an aperture 418 formed in a proximal portion 420 of the housing 410. The housing 410 can have a latch 422 that can facilitate selective attachment of the seal base 402 to the housing 410. When engaged, the latch 422 can secure the seal base 402 to the housing 410 such that the proximal flange 416 of the shield 406 is secured within the aperture 418 formed in the housing 410. When disengaged, the seal base 402 can be removed such that the shield 406 can be removed or adjusted as needed. In some embodiments, steering cables or another controlling mechanism known in the art can be used to control a position of the shield 406 and can be used to steer the shield 406 as needed along a tortuous pathway.

Figure 16A:
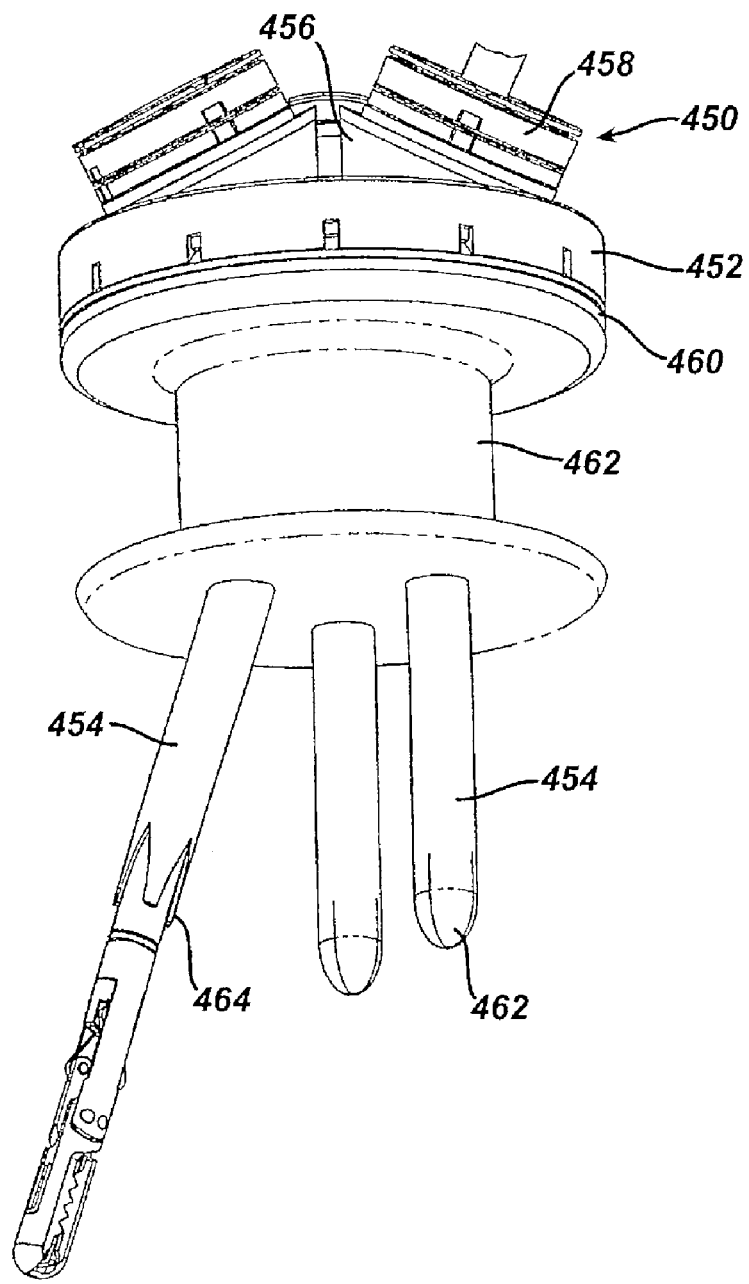
FIG. 16A is a perspective view of another embodiment of a surgical access device having sealing channels extending from each sealing port.
Figure 16B:
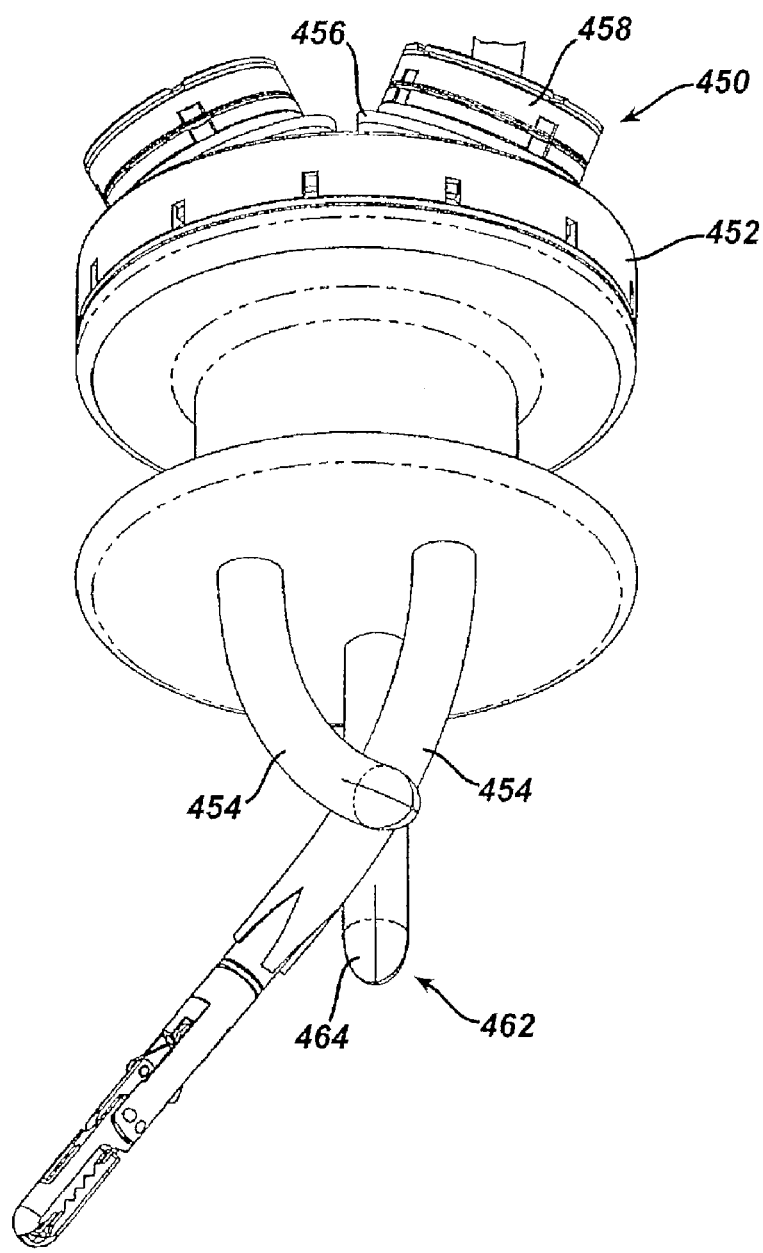
FIG. 16B is a perspective view of the surgical access device of FIG. 16A illustrating the flexibility of the seal channels.

In another embodiment, as shown in FIGS. 16A and 16B, each sealing port 450, a housing 460, a retractor 462, or the various devices disclosed herein can have a flexible elongate seal channel extending distally therefrom. The seal channel 454 can be removably attached to a closed distal surface of the retractor, or it can be directly coupled to a sealing element 458 and can extend through the seal base 452, the housing 460, the retractor 462, and beyond as needed. As shown in FIG. 16B, the seal channels 454 can be flexible such that the channels move with and maintain a seal around a surgical instrument inserted therethrough. A distal-most portion 462 of the sealing channel 454 can have sealing flaps 464 that can form a seal around a surgical instrument inserted therethrough that can remain closed when no instrument is inserted therethrough. Other exemplary embodiments of flexible seal channels are disclosed in U.S. Publication No. 2010/0081871, entitled "Surgical Access Device with Flexible Seal Channel," filed on Sep. 30, 2008, which is hereby incorporated by reference in its entirety.

Figure 17A:
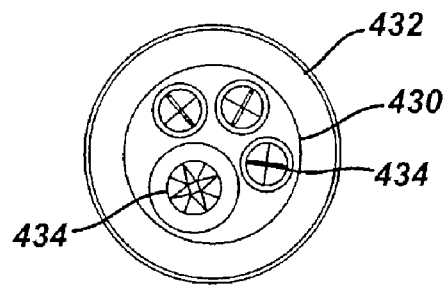
FIG. 17A is a top view of one embodiment of a seal base and a protective collar for use with a surgical access device.
Figure 17B:
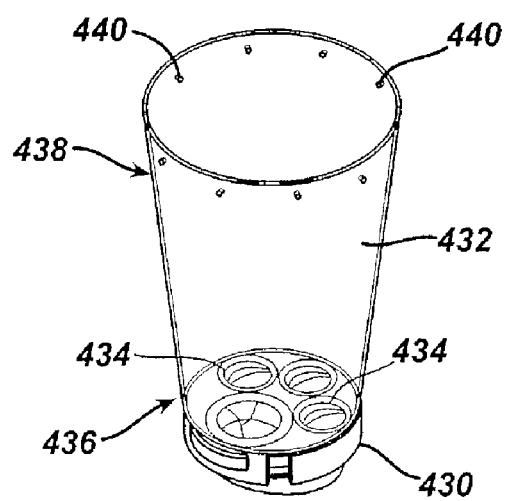
FIG. 17B is a perspective view of the seal base and the protective collar of FIG. 17A.
Figure 17C:
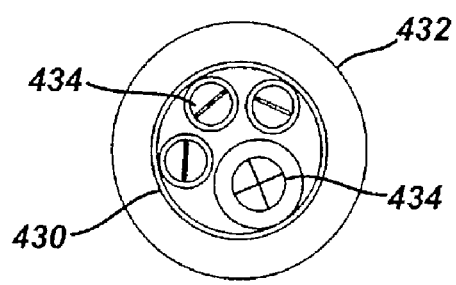
FIG. 17C is a bottom view of the seal base and the protective collar of FIG. 17A.

In another embodiment shown in FIGS. 17A-17C, a seal base 430 is provided having a collar or shield 432 extending proximally therefrom. The shield 432 can be configured to protect tissue as instruments are inserted into sealing ports 434. For example, a surgical access device could be inserted into an opening within a body that leaves tissue situated proximally of the seal base 430 exposed to punctures or tears by insertion of surgical instruments. Accordingly, the shield 432 can be attached to the seal base 430 and extend therefrom to provide protection to surrounding tissue.

The shield 432 can be attached to the seal base 430 by any attachment mechanism known in the art, and in one embodiment, the shield 432 can be connected to the seal base 430 using cantilevered snap tabs such that the shield is selectively removable as needed. The snaps and at least a distal portion 436 of the shield 432 can be substantially rigid to provide stability to the surgical access device. Any suitable material can be used to form the distal portion including, but not limited to polycarbonate or high density polyethylene. A proximal portion 438 of the shield 432 can be substantially flexible to allow maneuverability of the shield relative to tissue and can be formed of any suitable material known in the art including, but not limited to, silicone, urethane, thermoplastic elastomer, and rubber. In some embodiments, the shield 432 can have sufficient rigidity to allow it to be used to rotate the seal base 430 relative to a housing and/or a housing to rotate relative to a retractor.

In some embodiments, the shield 432 can have a series of apertures or openings 440 formed around a circumference of the proximal portion 438. The openings 440 can allow the shield 432 to be secured to a patient using sutures or other mechanisms and/or to secure a modesty covering for a patient. In addition, stability features, for example ridges or grooves, can be located on a tissue contacting surface of the shield 432 to prevent rotation of the shield 432 once inserted into a patient. A person skilled in the art will appreciate that various shapes and types of shields, both rigid and flexible, can be used in various positions within a surgical access device to protect various components and/or tissue.

Figure 17D:
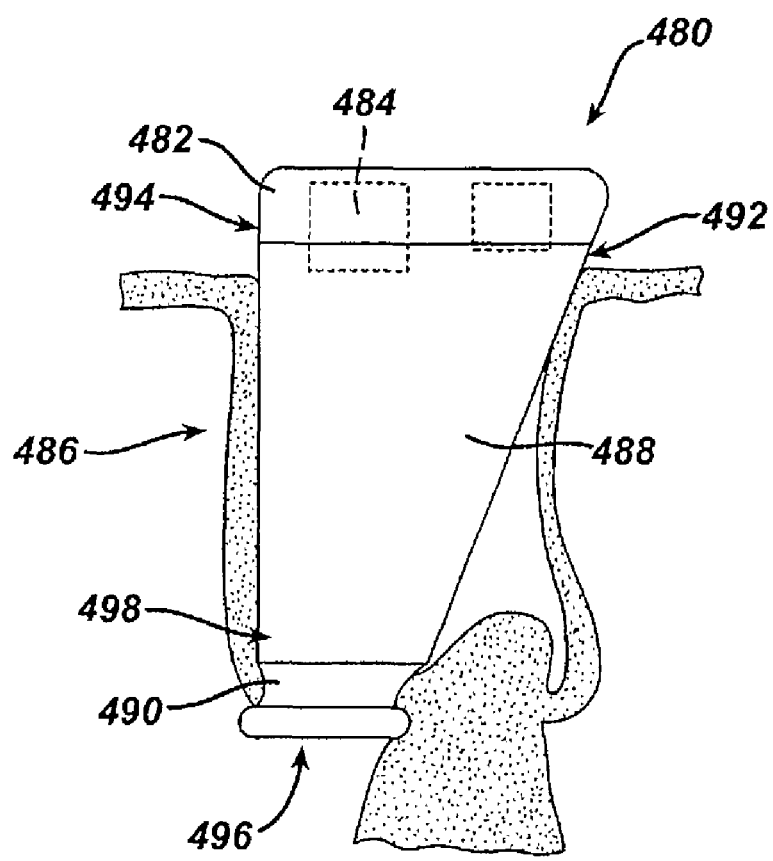
FIG. 17D is a side view of one embodiment of a retractor having a collar providing access to a recessed opening in a patient's body.

In another embodiment, the shield can extend between the housing and the retractor, and it can vary in shape. For example, FIG. 17D illustrates a surgical access device 480 having a housing 482 with a variety of sealing ports 484 formed therethrough. The housing 482 has an extended retractor 486 formed from a conically shaped collar 488 and a flexible elongate portion 490. A proximal portion 492 of the collar 488 can be fixedly or movably mated with a distal portion 494 of the housing 482 by any mating mechanism known in the art, for example, adhesive, press fit, etc. The collar 488 can be flexible or rigid and can have any length as needed to provide a working channel to a recessed opening 496 in a patient's body such that the flexible elongate portion 490 can be positioned therein. The flexible elongate portion 490 can extend through the collar 488, or it can be formed on or mated to a distal end 498 of the collar 488 and can extend distally therefrom. In some embodiments, the flexible elongate portion 490 can have a portion that extends past the wall of the vagina and further into the abdomen, either with or without a distal ring. As shown, the collar 488 can have a diameter that decreases distally to provide a particular fit within an opening and/or along a specific pathway into the body. In some embodiments, the collar 488 can have openings formed therein to allow tissue to invaginate into the collar 488 to retain the flexible elongate portion 490. It will be appreciated by those skilled in the art that the collar 488 can have any shape or angular orientation as needed to provide access to a recessed opening in a patient's body. In this way, the flexible elongate portion 490 can function to hold open the recessed opening 496 while the collar 488 provides a pathway from the housing 482 to the flexible elongate portion 490 such that surgical instruments can be inserted therethrough for various procedures within a patient's body.

In any and all of the surgical access device embodiments disclosed herein, an engagement and/or release mechanism can be included to allow a seal base to be separated from a housing, to allow a housing to be separated from a retractor, and/or to allow a seal port to be separate from a seal base. In one embodiment shown in FIGS. 18A-18F, a surgical access device 500 is provided and can include a seal cap 514 having openings 506 formed therein and a seal base 502 with one or more sealing ports 504 in communication with the openings 506 of the seal cap 514. The sealing ports 504 can have one or more sealing elements 512 therein. A housing 508 can seat and support the seal cap 514 and the seal base 502, and a retractor 510 can be mated with the housing 508 and can be configured to be positioned within an opening in a patient's body.

As shown, the seal cap 514 and the housing 508 can include an engagement and release mechanism in the form of a latch mechanism 516 that enables the seal cap 514 to be removable from the housing 508. Two tabs 518 can extend from opposite sides of a distal portion 520 of the seal cap 514 and can be configured to engage corresponding slots 522 formed in an inner ring 524 of the housing 508. A latch ring 526 can be positioned between the inner ring 524 and an outer circumference of the housing 508 and can have a latch 528 formed thereon. The latch 528 can extend outward from the latch ring 526 through a window 530 in the outer circumference of the housing 508 and can be moved laterally back and forth a short distance within the window 530, as will be described in more detail below.

Figure 18A:
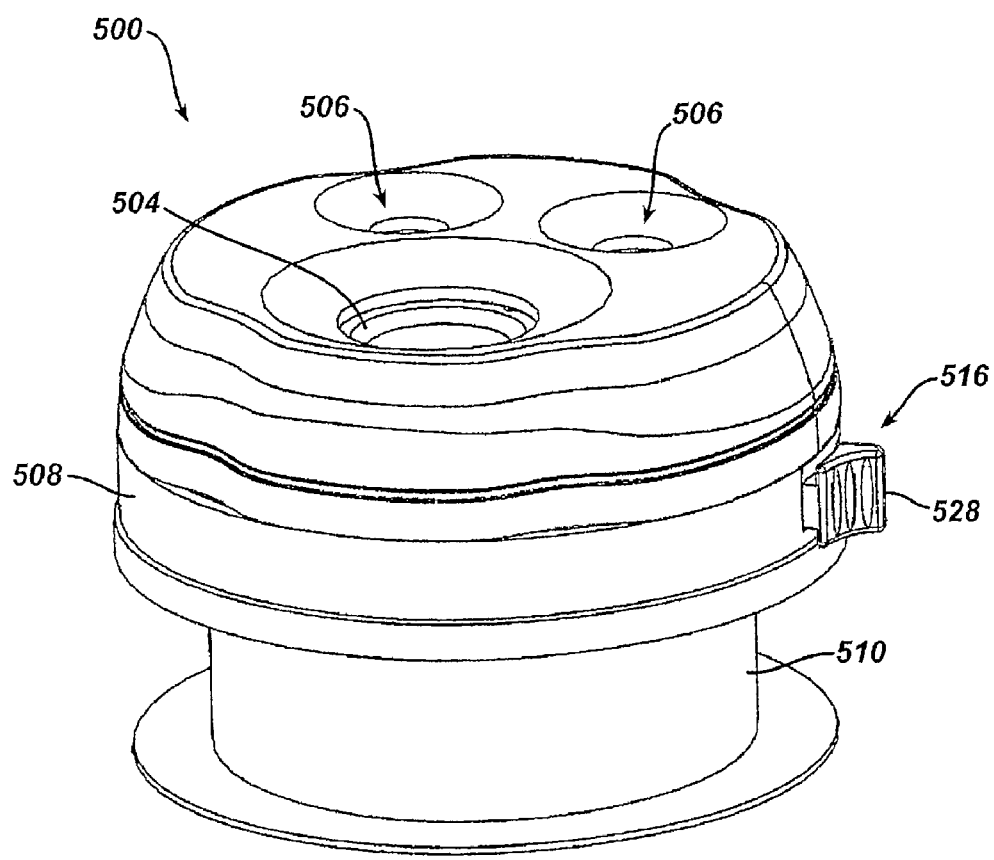
FIG. 18A is a perspective view of one embodiment of a latching mechanism for use in a surgical access device.
Figure 18B:
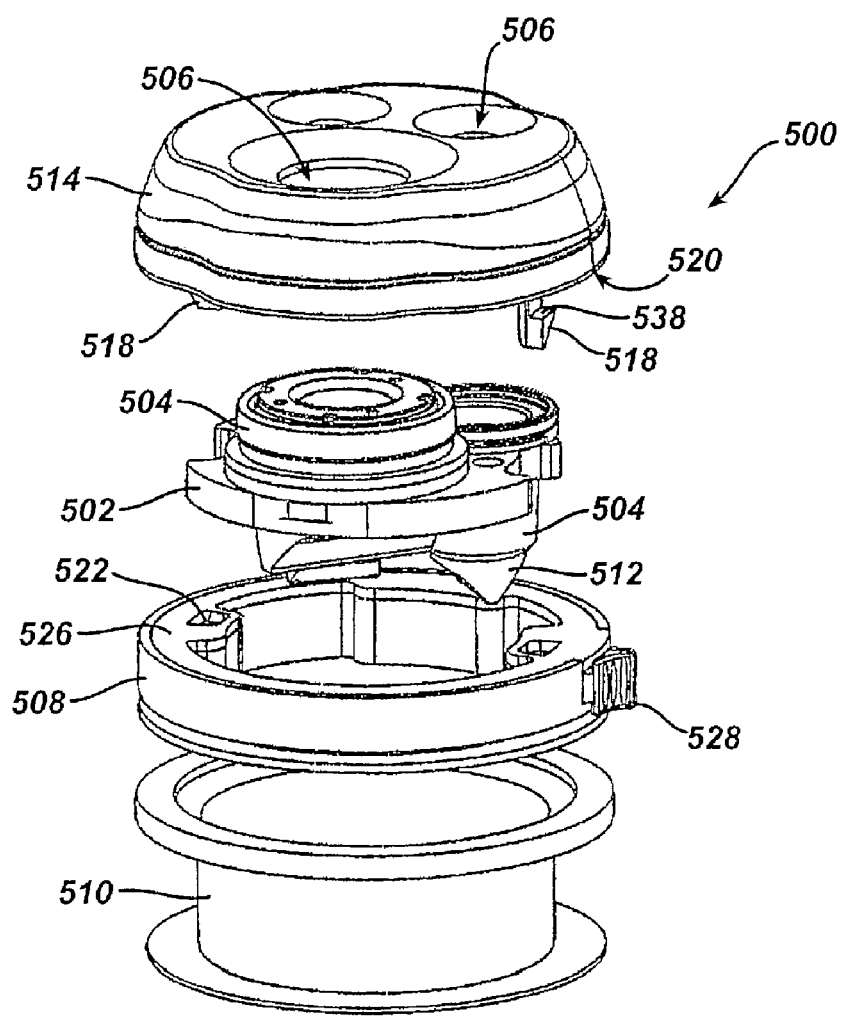
FIG. 18B is an exploded view of the latching mechanism of FIG. 18A.
Figure 18C:
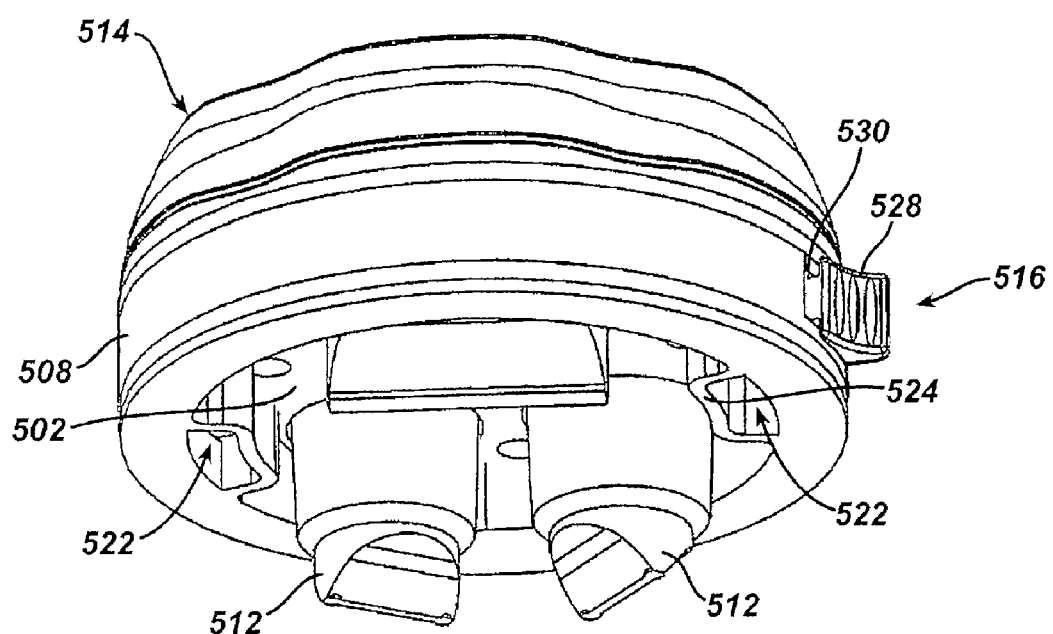
FIG. 18C is another perspective view of the latching mechanism of FIG. 18A.
Figure 18D:
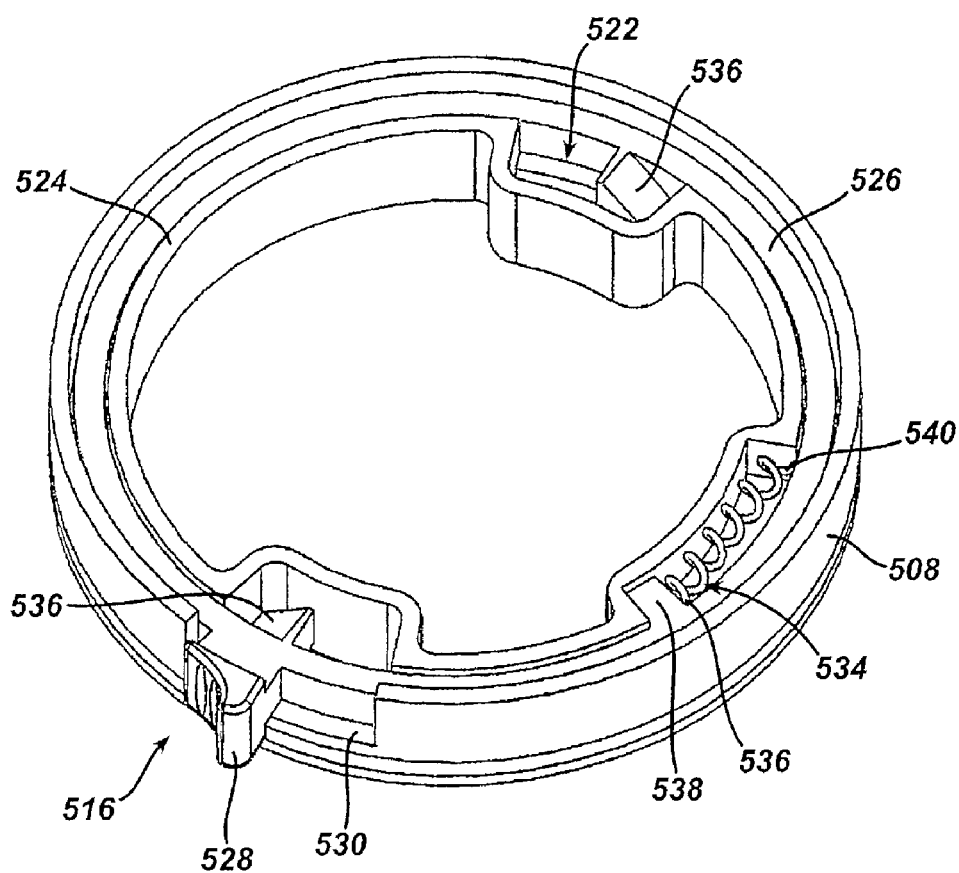
FIG. 18D is a perspective view of a housing for use in the latching mechanism of FIG. 18A.
Figure 18E:
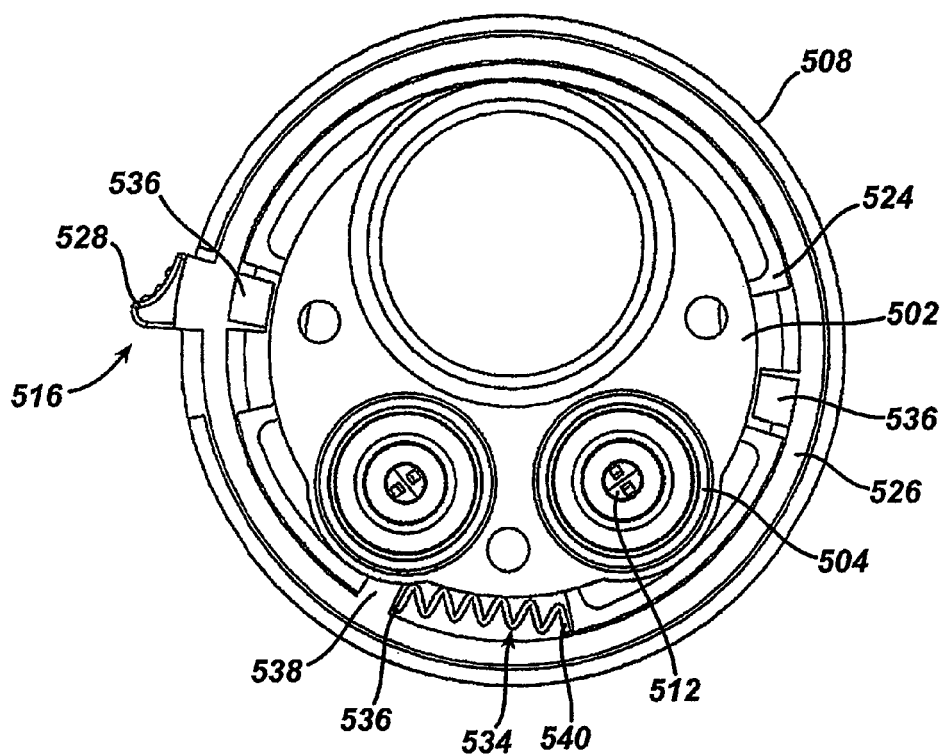
FIG. 18E is a bottom view of the housing and a seal base for use in the latching mechanism of FIG. 18A.

The inner ring 524 can include a spring slot 532 for receiving a spring 534 therein. One end 536 of the spring 534 can be in contact with a protrusion 538 of the latch ring 526. An opposing end 540 of the spring 534 can be in contact with the spring slot 532 of the inner ring 524. In this way, as the latch 528 is moved within the window 530, the entire latch ring 526 moves, thereby causing the spring to be compressed between the protrusion 538 and one end of the spring slot 532. Accordingly, the latch 528 is biased to a position in which the spring 534 is uncompressed, as shown in FIG. 18D.

As the tabs 518 on the seal cap 514 are inserted into the slots 522 in the housing 508, the tabs 518 can engage camming elements 536 and thereby cause the latch 528 to move laterally within the window 530 as the latch ring 526 is moved relative to the outer circumference of the housing 508 and the inner ring 524. Once the tabs 518 are inserted past ledges 538 formed on the tabs 518, the spring 534 can cause camming elements 536, and correspondingly the latch 528, to travel back to their biased position shown in FIG. 18D, thereby securing the seal cap 514 to the housing 508. To release the seal cap 514 from the housing 508, the latch 528 can be moved laterally within the window 530 to cause the protrusion 538 in the latch ring 526 to compress the spring 534. This action can move the camming element 536 out of the way of the tabs 518, thereby allowing the seal cap 514 to be disengaged and withdrawn from the housing 508. In this way the latch mechanism 516 can allow for repeated engagement and disengagement of seal caps and seal bases from a housing and retractor as needed.

Figure 19A:
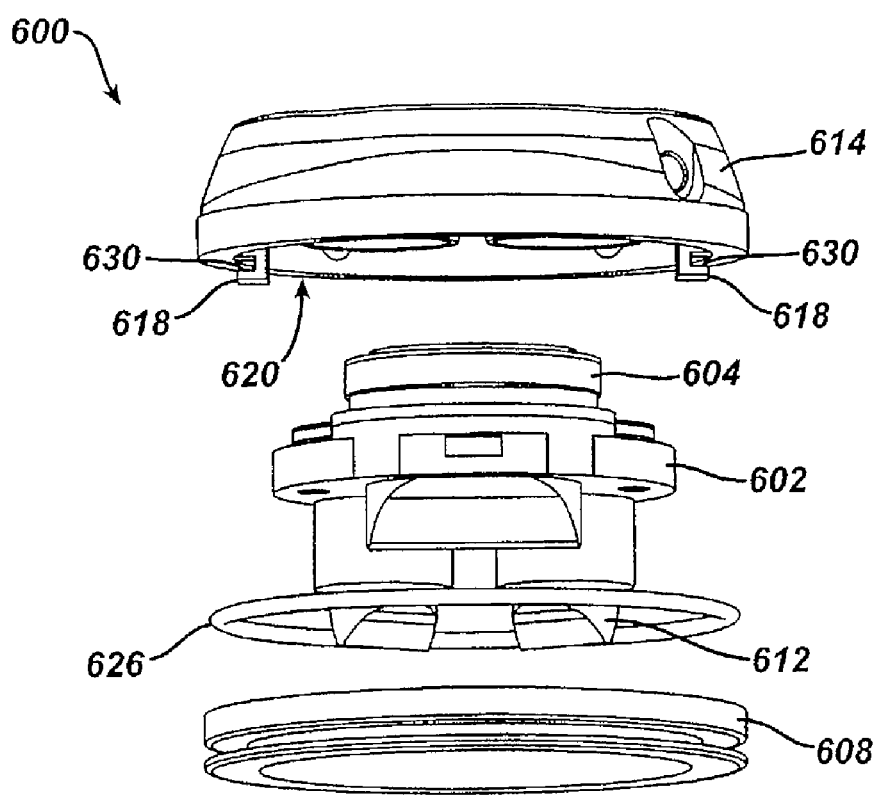
FIG. 19A is an exploded view of another embodiment of a latching mechanism for use in a surgical access device.
Figure 19B:
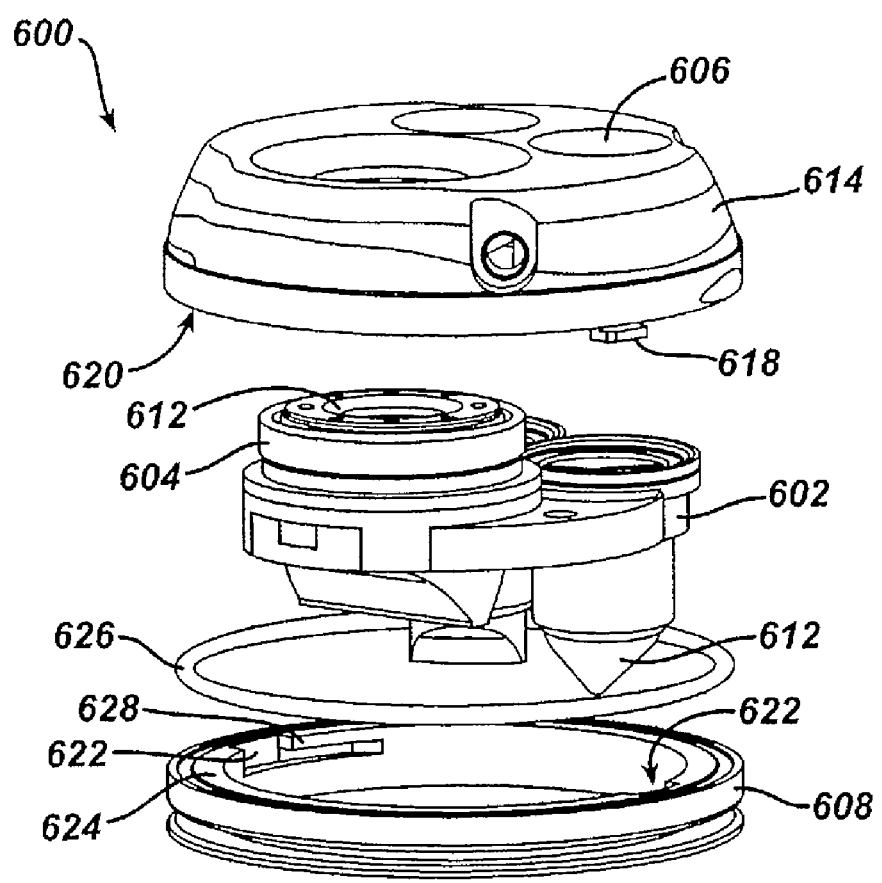
FIG. 19B is another exploded view of the latching mechanism of FIG. 19A.

In another embodiment shown in FIGS. 19A and 19B, a proximal portion 600 of a surgical access device is provided and can include a seal cap 614 having openings 606 formed therein and a seal base 602 with one or more sealing ports 604 in communication with the openings 606 of the seal cap 614. The sealing ports 604 can have one or more sealing elements 612 therein. A housing 608 can seat and support the seal cap 614 and the seal base 602, and a retractor (not shown) can be mated with the housing 608 and can be configured to be positioned within an opening in a patient's body. An o-ring 626 can be positioned between the seal cap 614 and the housing 608 to ensure an air and liquid tight seal therebetween.

As shown, the seal cap 614 and the housing 608 can include an engagement and release mechanism in the form of a bayonet latch mechanism. Two bayonet feet 618 can extend from opposite sides of a distal portion 620 of the seal cap 614 and can be configured to engage corresponding slots 622 formed in an inner ring 624 of the housing 608. The bayonet feet 618 on the seal cap 614 can be lowered into the slots 614 in the inner ring 624 of the housing 608. The seal cap 614 can be rotated, for example in a clockwise direction, relative to the housing 608, thereby causing the bayonet feet 618 to travel laterally within the slots 622 to a position in which ledges 628 cover corresponding ledges 630 on the bayonet feet 618, thereby securing or locking the seal cap 614 to the housing 608. If disengagement is desired, the seal cap 614 can be rotated, for example in a counter clockwise direction, such that the bayonet feet 618 are free to be withdrawn from the slots 614.

Figure 20A:
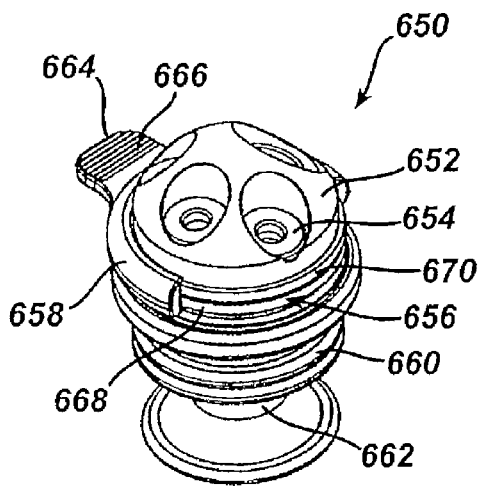
FIG. 20A is a perspective view of one embodiment of a surgical access device having a C-clamp securing mechanism.
Figure 20B:
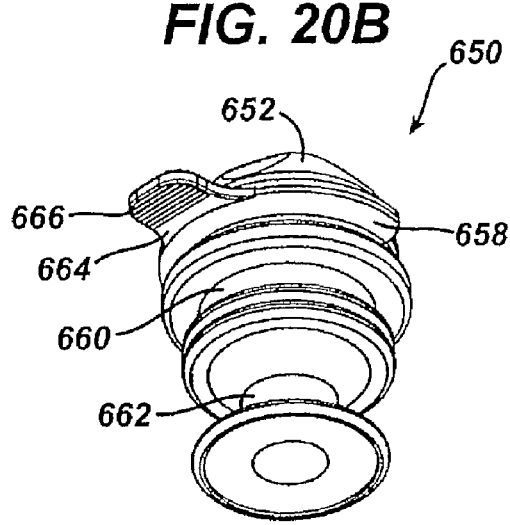
FIG. 20B is a perspective view of the surgical access device embodiment of FIG. 20A.
Figure 20C:
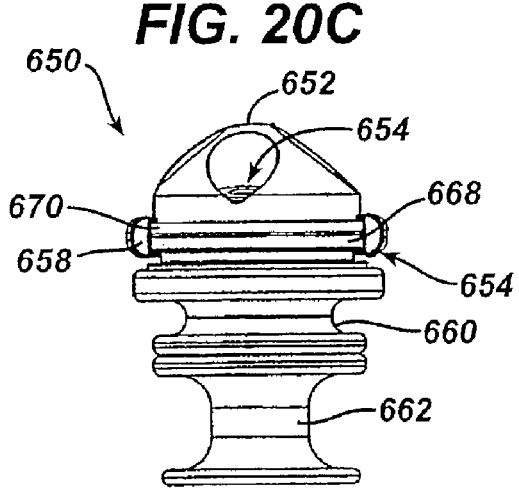
FIG. 20C is a perspective view of the surgical access device embodiment of FIG. 20A.

In a further embodiment shown in FIGS. 20A-20C, a surgical access device 650 is provided having a dome-shaped seal base 652 with a plurality of seal ports 654 extending therethrough. The seal base 652 can be positioned adjacent to a housing 656 and secured thereto by a C-clamp 658. A first retractor 660 can be mated with the housing 656 by any method known in the art and a second retractor 662 can be mated with the first retractor 660 as shown.

The C-clamp 658 can be a substantially rigid element that is in the shape of a "C" and can have a tab 664 formed integrally therewith. The tab 664 can have a series of ridges 666 or other surface formations that allow for an easy and secure grip during attachment and removal of the C-clamp 658. The C-clamp 658 can be positioned around a proximal rim 668 of the housing 656 and a distal rim 670 of the seal base 652 to thereby secure the two together. The C-clamp 658 provides a press-fit around the rims 668, 670. The C-clamp 658 can be removed from around the two rims 668, 670 to allow detachment of the seal base 652 from the housing 656. A person skilled in the art will appreciate that a variety of clamps can be used to secure various components of the surgical access devices together as needed.

There are various features that can optionally be included with any and all of the surgical access device embodiments disclosed herein. For example, a component of the device, such as a seal base, housing, retractor, etc., can have one or more lights formed thereon or around a circumference thereof to enable better visualization when inserted within a patient. As will be appreciated, any wavelength of light can be used for various applications, whether visible or invisible. Any number of ports can also be included on and/or through the surgical access devices to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

The embodiments described herein can be used in any known and future surgical procedures and methods, as will be appreciated by those skilled in the art. For example, any of the embodiments described herein can be used in performing a sleeve gastrectomy and/or a gastroplasty, as described in U.S. Publicaion No. 2010/008163, entitled "Methods and Devices for Performing Gastrectomies and Gastroplasties," on Sep. 30, 2008, U.S. Publication No. 2010/0081864, entitled "Methods and Devices for Performing Gastrectomies and Gastroplasties," filed on Sep. 30, 2008, and U.S. Publication No. 2010/0081883, entitled "Methods and Devices for Performing Gastroplasties Using a Multiple Port Access Device," filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
    a housing having a flexible base with a plurality of rigid sealing ports extending therethrough, each sealing port having a sealing element therein, the flexible base being movable to allow each sealing port to selectively position instruments extending through the sealing element at converging and diverging positions relative to one another, wherein the base has a resting position in which the base has a non-planar substantially convex configuration extending across the housing such that a proximal-most end of each sealing port is distal to a proximal-most end of the housing.

2. The surgical access device of claim 1, wherein the flexible base is movable between the substantially convex configuration and a substantially concave configuration.

3. The surgical access device of claim 1, wherein each sealing port within the housing is selectively movable between a proximal position within the housing and a distal position within the housing.

4. The surgical access device of claim 1, further comprising a retractor extending distally from the housing and configured to form an opening through tissue for receiving instruments inserted through the sealing ports.

5. The surgical access device of claim 4, wherein the housing includes a distal annulus that releasably couples to a proximal flange on the retractor.

6. The surgical access device of claim 4, wherein the housing is rotatable relative to the retractor.

7. The surgical access device of claim 4, further comprising a flexible connector extending between the housing and the retractor to allow the housing to move relative to the retractor.

8. The surgical access device of claim 4, wherein the housing is hingedly connected to the retractor.

9. The surgical access device of claim 4, further comprising a release mechanism configured to allow selective engagement and disengagement of the housing with the retractor.

10. The surgical access device of claim 4, further comprising a flexible shield disposed within the retractor and configured to protect the retractor from damage caused by insertion of surgical instruments through the sealing ports and the retractor.

11. The surgical access device of claim 4, wherein the retractor includes a lighting element disposed thereon to allow illumination of a body cavity.

12. The surgical access device of claim 1, wherein each sealing port has a central axis that differs from one another and that differs from a central longitudinal axis of the housing.

13. The surgical access device of claim 1, wherein at least one of the sealing ports has an opening with a diameter different than a diameter of an opening in the other sealing ports.

14. The surgical access device of claim 1, wherein at least one of the sealing ports has a non-circular opening and is rotatable relative to the flexible base.

15. The surgical access device of claim 1, wherein each sealing port includes at least one of an instrument seal configured to form a seal around an instrument inserted therethrough, and a channel seal configured to seal the access port when no instrument is inserted therethrough.

16. A surgical access device, comprising:
a housing having a retractor extending therefrom and configured to form a pathway through tissue and a plurality of rigid sealing ports having sealing elements therein for receiving surgical instruments therethrough, each sealing port being freely movable relative to one another, relative to the housing, and relative to tissue when the retractor is positioned in tissue such that a proximal-most end of each sealing port is movable between a position outside of the housing and a position within the housing.

17. The surgical access device of claim 16, wherein each sealing port is disposed in a flexible base coupled to the housing.

18. The surgical access device of claim 17, wherein the flexible base is movable between convex and concave positions to move the sealing ports.

19. The surgical access device of claim 16, wherein each sealing port freely moves laterally, vertically, rotationally, and combinations thereof.

20. The surgical access device of claim 16, wherein the housing is rotatable relative to the retractor.

21. The surgical access device of claim 16, wherein each sealing port has a central axis that differs from one another and that differs from a central longitudinal axis of the housing.

22. The surgical access device of claim 16, further comprising a connector extending between the housing and the retractor to allow the housing to move relative to the retractor.

23. The surgical access device of claim 16, further comprising a release mechanism configured to allow selective engagement and disengagement of the housing with the retractor.

24. The surgical access device of claim 16, further comprising a flexible shield disposed within the retractor and configured to protect the retractor from damage caused by insertion of surgical instruments through the sealing ports and the retractor.

25. A surgical access device, comprising:
a housing having a plurality of sealing ports for receiving surgical instruments;
a retractor having an opening formed therethrough for providing a pathway through tissue for surgical instruments inserted through the plurality of sealing ports; and
a flexible connector configured to extend and compress in length, the connector being coupled between a distal end of the housing and a proximal end of the retractor that allows the housing to have a full range of lateral and vertical motion relative to the retractor.

26. The surgical access device of claim 25, wherein the connector allows rotational motion of the housing relative to the retractor.

27. The surgical access device of claim 25, wherein the connector has a proximal flange and a distal flange and a flexible cylindrical portion extending therebetween.

28. The surgical access device of claim 25, wherein the connector is formed from an elastomeric material.

29. The surgical access device of claim 25, wherein the housing is rotatable relative to the connector.

30. The surgical access device of claim 25, wherein at least one sealing port is rotatable relative to the housing.

31. The surgical access device of claim 25, wherein each sealing port has a central axis that differs from one another and that differs from a central longitudinal axis of the housing.

32. The surgical access device of claim 25, further comprising a flexible shield disposed within the retractor and configured to protect the retractor from damage caused by insertion of surgical instruments through the sealing ports and the retractor.

* * * * *